Figure 1:
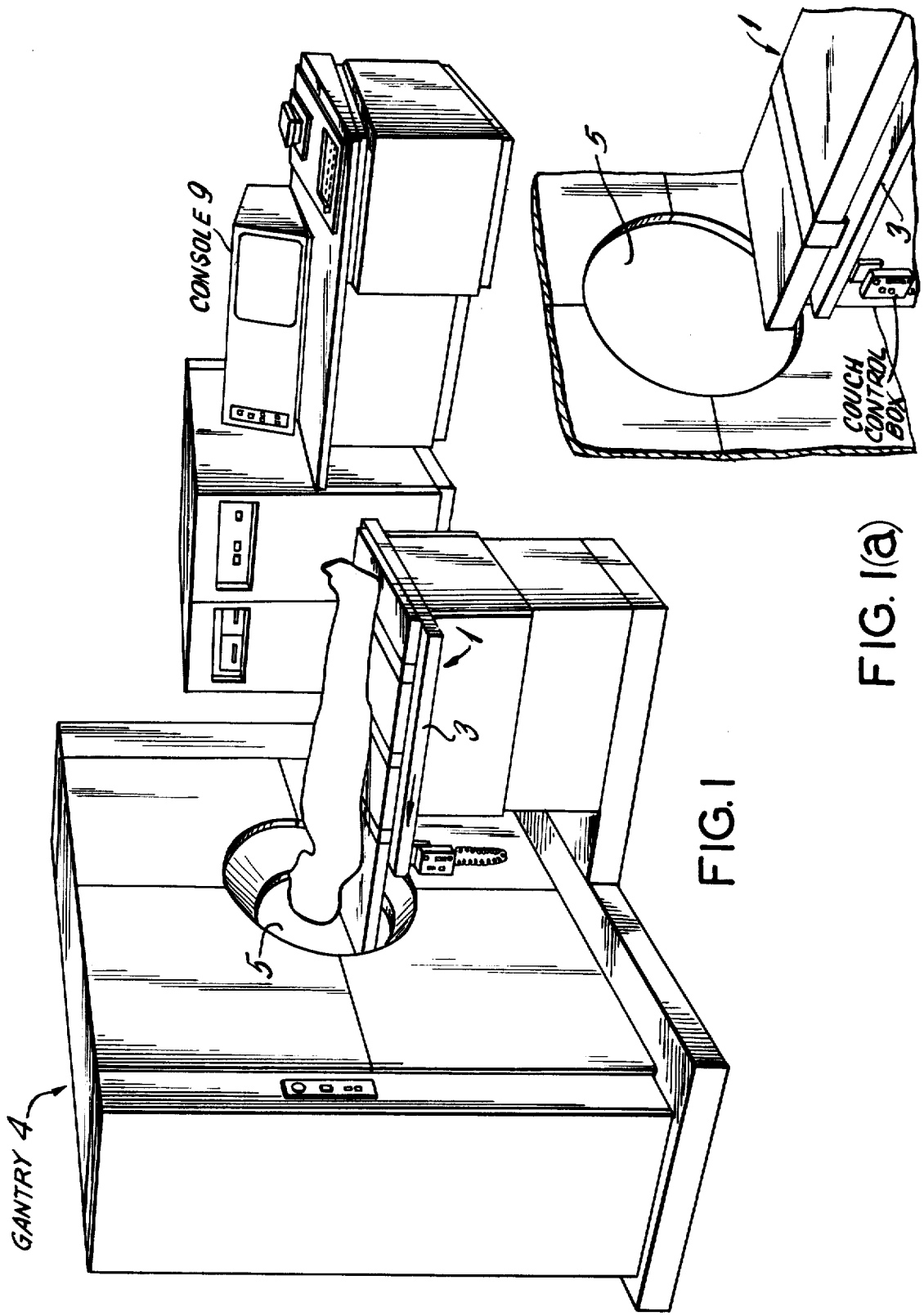

United States Patent [19]

Carman et al.

[11] 4,195,227
[45] Mar. 25, 1980

[54] WHOLE BODY IMAGING SYSTEM MECHANISM

[75] Inventors: Richard W. Carman, Foxboro; Edward J. Doherty, III, Halifax, both of Mass.

[73] Assignee: Union Carbide Corporation, New York, N.Y.

[21] Appl. No.: 917,356

[22] Filed: Jun. 20, 1978

[51] Int. Cl.² .................................................. G02B 5/00
[52] U.S. Cl. .................................. 250/505; 250/445 T; 250/515

[58] Field of Search .................... 250/505, 445 T, 515

[56] References Cited

U.S. PATENT DOCUMENTS 3,997,794  12/1976  York et al. .......................... 250/505

Primary Examiner—Harold A. Dixon
Attorney, Agent, or Firm—Frederick J. McCarthy, Jr.

[57] ABSTRACT

Scanning apparatus is provided for a movable array of highly focused collimators surrounding a scan field.

1 Claim, 53 Drawing Figures

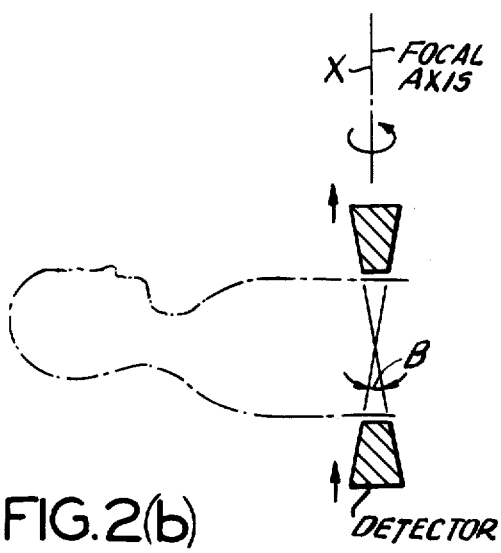
FIG.2(b)
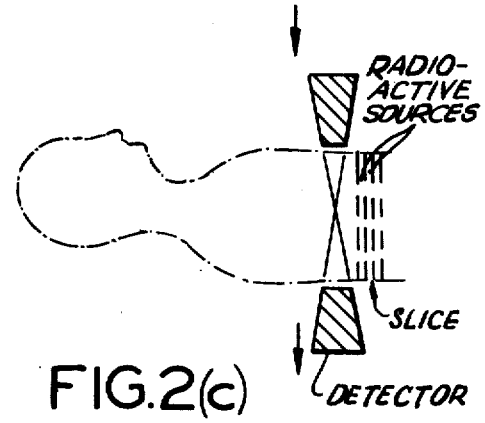
FIG.2(c)
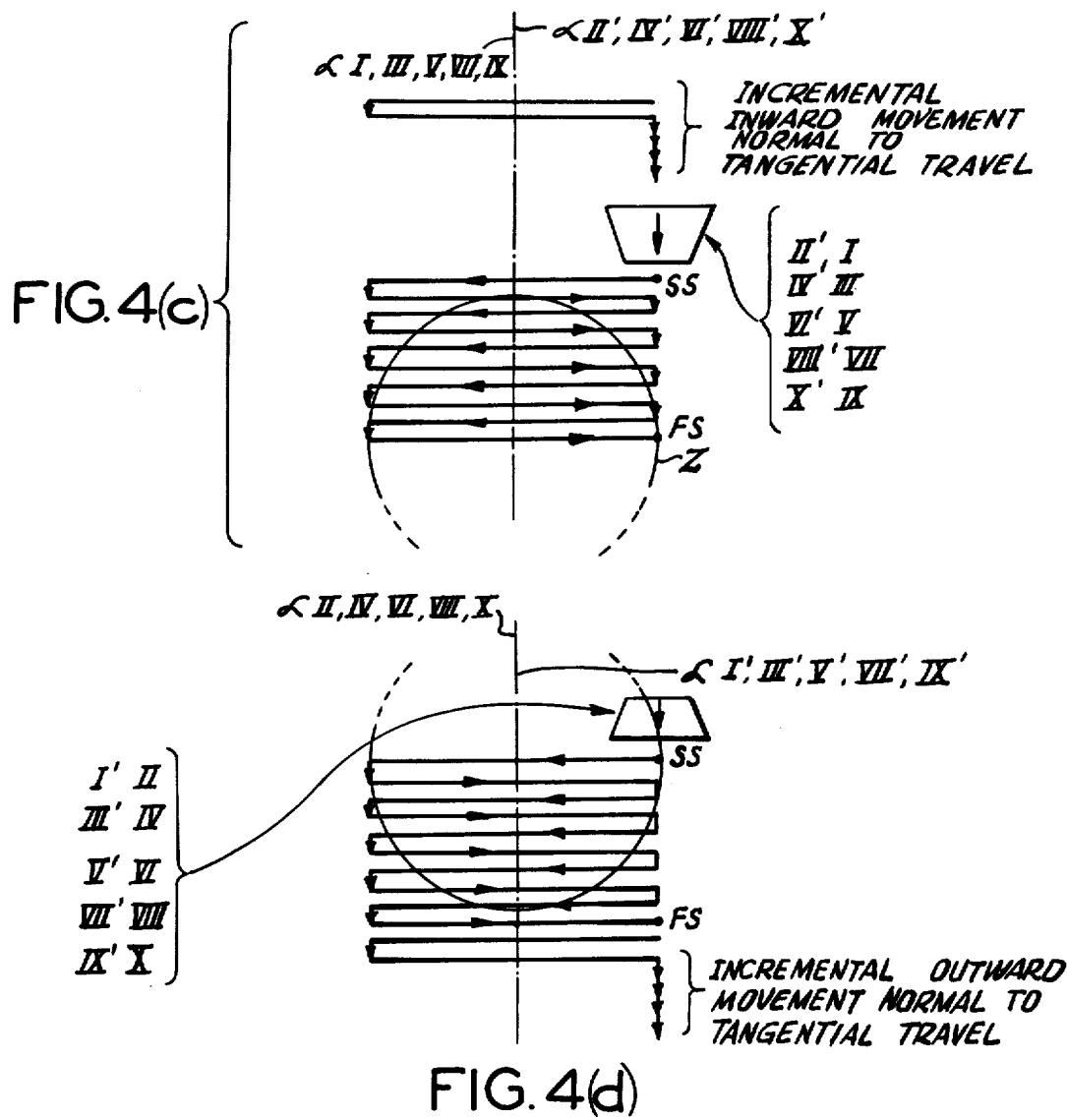
FIG.4(c)
FIG.4(d)

```
PATIENT 005        TIME(PI) 60
RADIONUCLIDE 99    DOSE 5
DATE    6/ 2/78    HOSP UCIS
SLICE NO. 7        SPACING  6/8
SCAN TIME  5       NO. SLICES 8
WINDOW  51%/ 11%   ENHANCE   1
```

FIG. 8

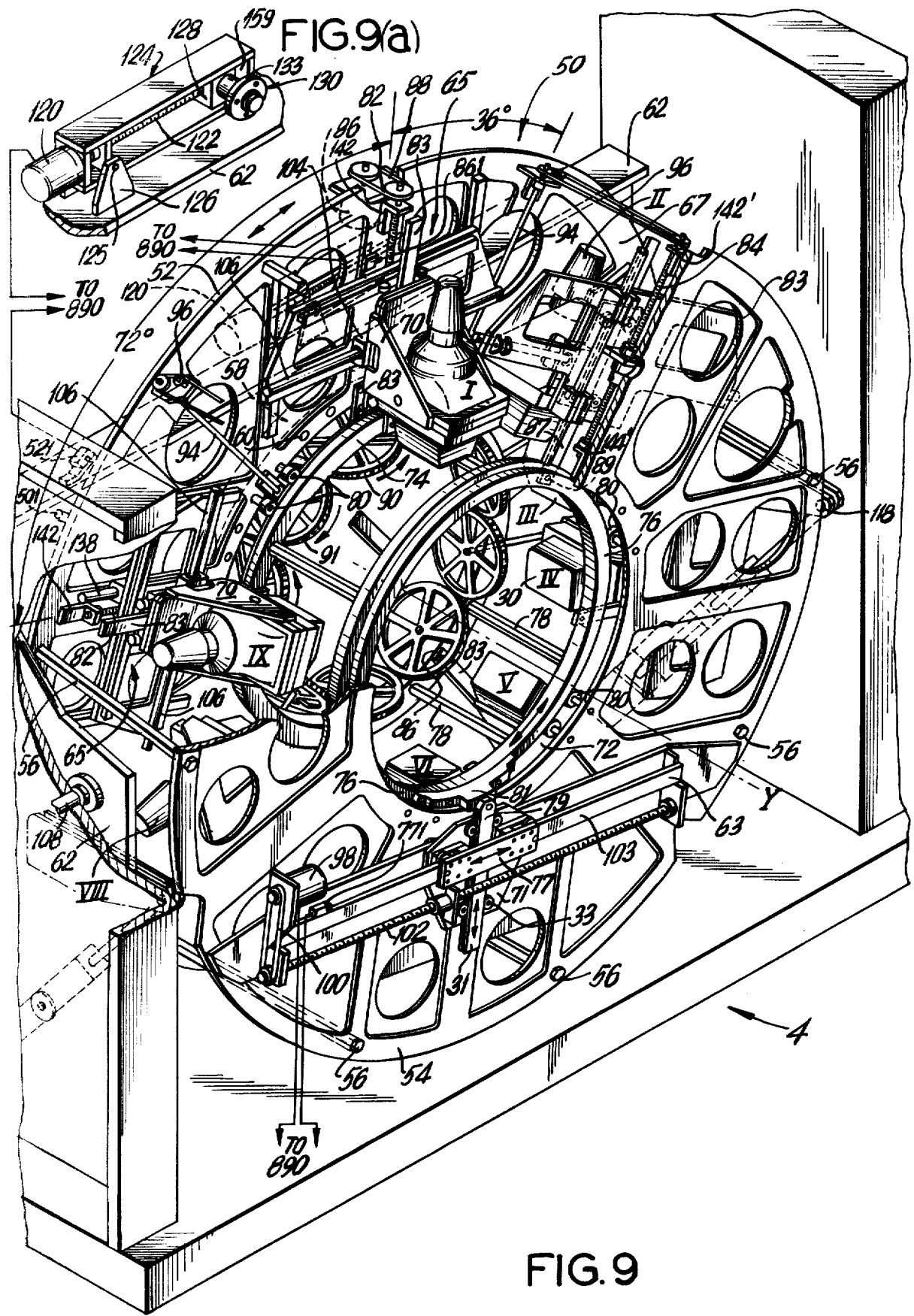

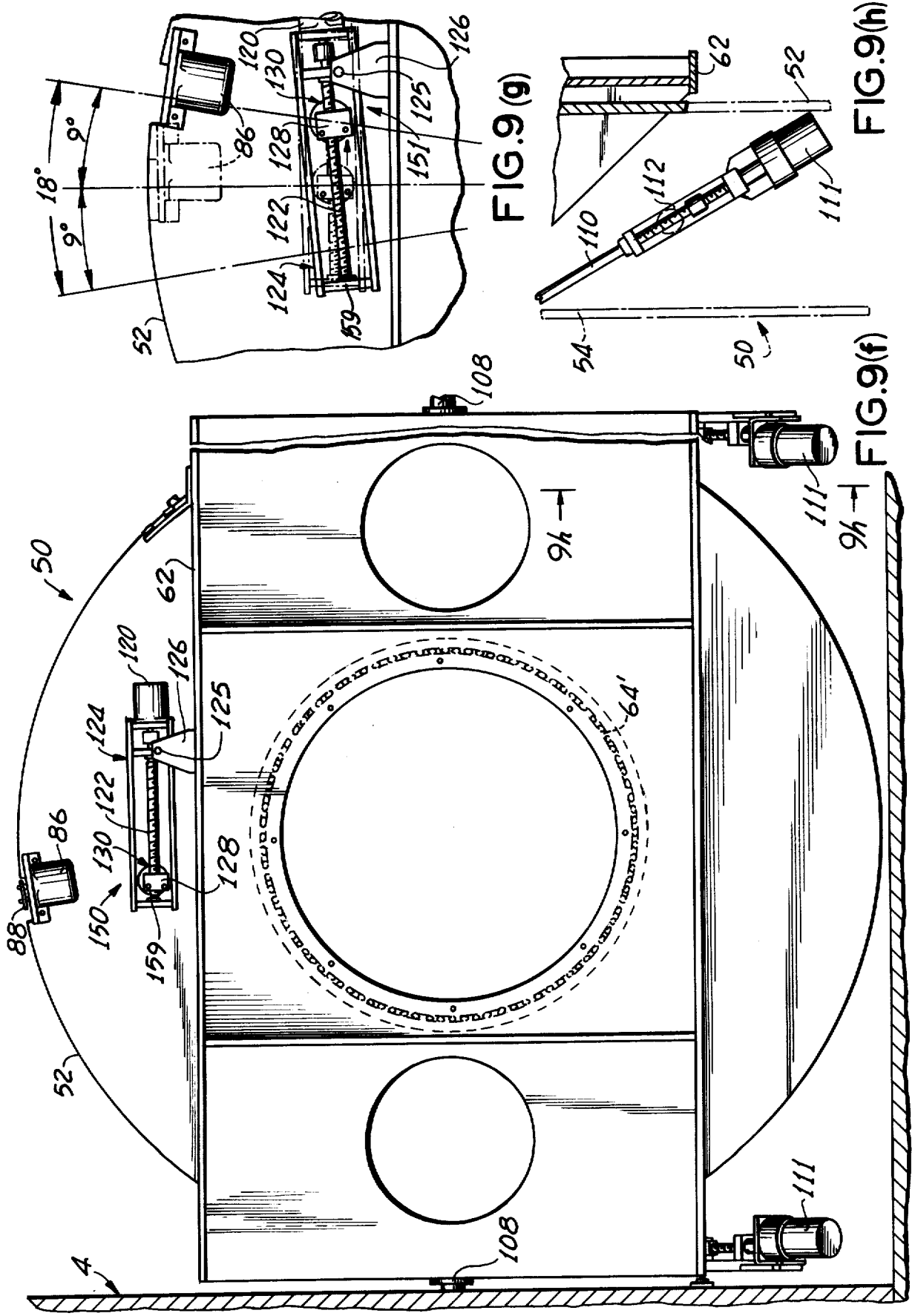

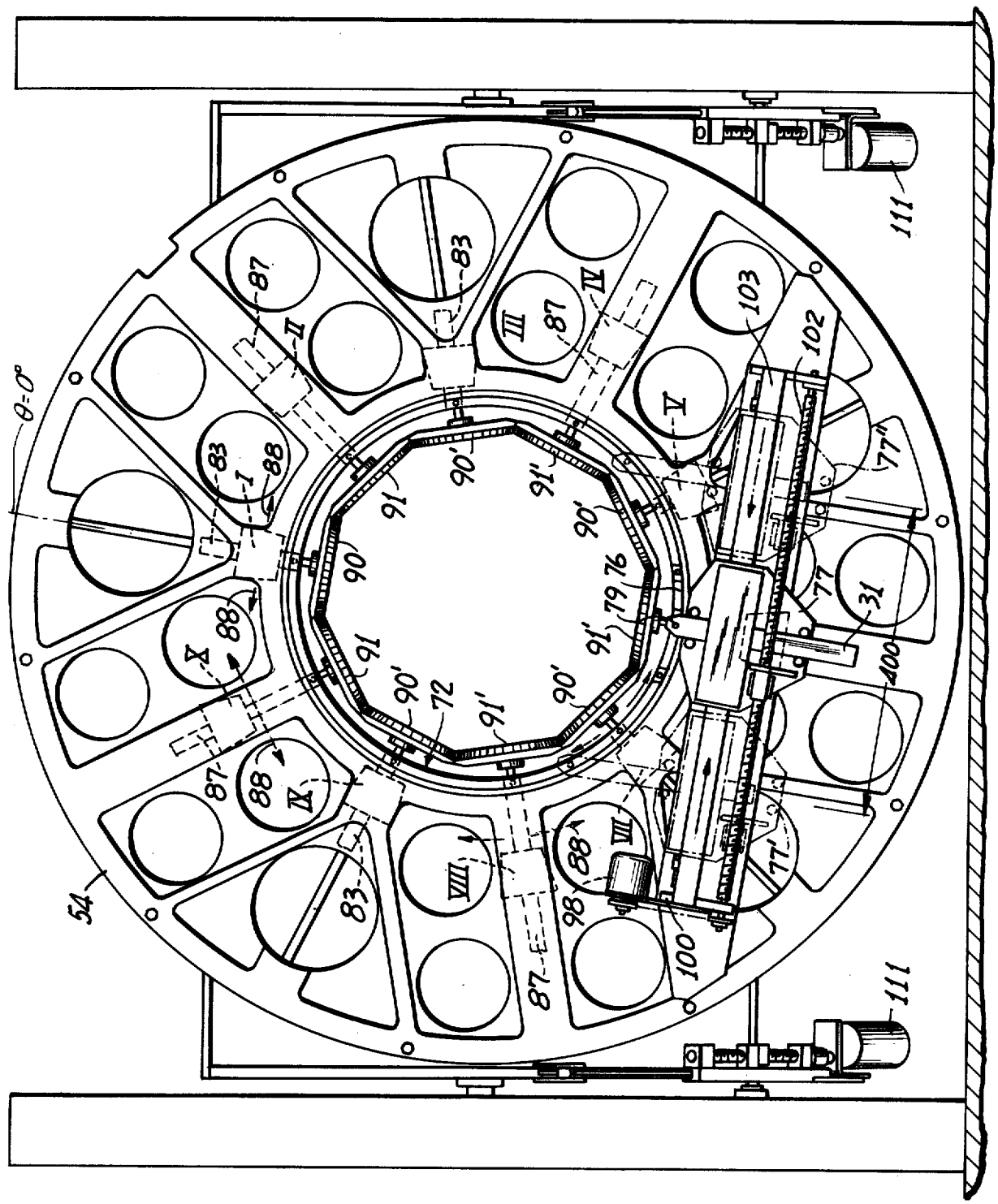

TIMING DIAGRAM FOR TRANSFERRING DATA FROM SCANNER DATA MULTIPLEXER INTO COMPUTER MEMORY

TIMES SHOWN IN NANOSECONDS

FIG.13

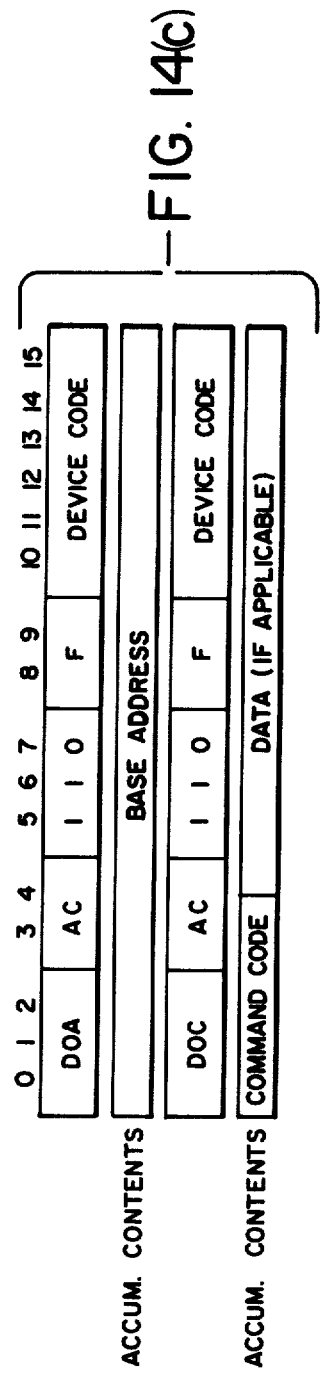
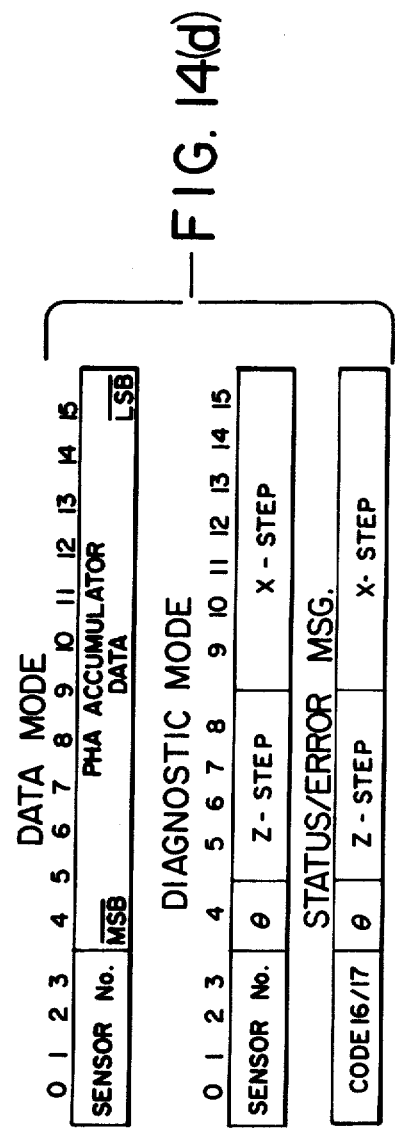
FIG. 14(a)
FIG. 14(b)
FIG. 14(c)
FIG. 14(d)

WHOLE BODY IMAGING SYSTEM MECHANISM

This invention relates to nuclear medicine. More particularly the present invention relates to an imager which very effectively enables the high sensitivity quantification and spatial location of the radioactivity of a body section of a patient who has been administered material tagged with radionuclides.

In the field of nuclear medicine, the importance of imaging has been recognized and the subject has been studied and investigated. See for example, "What is the Role of Nuclear Medicine in Medical Imaging" Edward M. Smith Sc. D., Maryville, Tennessee*; "Physics and Instrumentation"—Thomas F. Budinger and F. David Rollo "Progress in Cardiovascular Diseases", Vol. XX, No. 1 July/August 1977 pp 19–53; "Emission Computer Assisted Tomography with Single-Photon and Positron Annihilation Photon Emitters"—Thomas F. Budinger, Stephen E. Derenzo, Grant T. Gulberg, William L. Greenberg and Ronald H. Huesman.** Also, U.S. Pat. No. 3,970,853—David E. Kuhl and Roy Q. Edwards "Transverse Section Radionuclide Scanning System" has described a scanning system for obtaining in vivo transverse sections of the brain of radionuclide administered patient. The scanning system in the Kuhl et al patent utilizes mildly focused collimators arranged in a rotating picture frame arrangement of offset interlaced radiation detectors. In the Kuhl et al system a "fat pencil" of sensitivity is utilized, and this system, while representing a significant contribution in the art of imaging, does not enable the desired optimal high degree of spatial resolution and sensitivity. Other techniques, utilizing "narrow pencils" or sensitivity, in order to improve spatial resolution, are even more hampered by what can be considered an imperative of nuclear medicine, i.e. the collection of a maximum amount of patient emitted radiation, e.g. gamma ray photons, during the short period of time which is compatible with patient immobility. Other efforts which employ gamma cameras and "parallel hole" collimators to simultaneously record many "narrow pencils" of radiation have been subject to similar difficulties. U.S. patent application Ser. No. 865,894 "Nuclear Transverse Sectional Brain Function Imager", H. F. Stoddart, describes an imager using highly focused collimators which is highly effective in providing rapid, high-sensitivity quantification and spatial location of the radioactivity of a body organ in a transverse section.

* South Eastern Chapter, Society of Nuclear Medicine Continuing Education 1976.
** Journal of Computer Assisted Tomography Vol. 1, No. 1, 1977.

It is an object of the present invention to provide a transverse section imager for use in nuclear medicine which rapidly collects emitted radiation from a transverse body section and enables a rapid, high sensitivity quantification and spatial location of the radioactivity of the body section.

Figure 2:
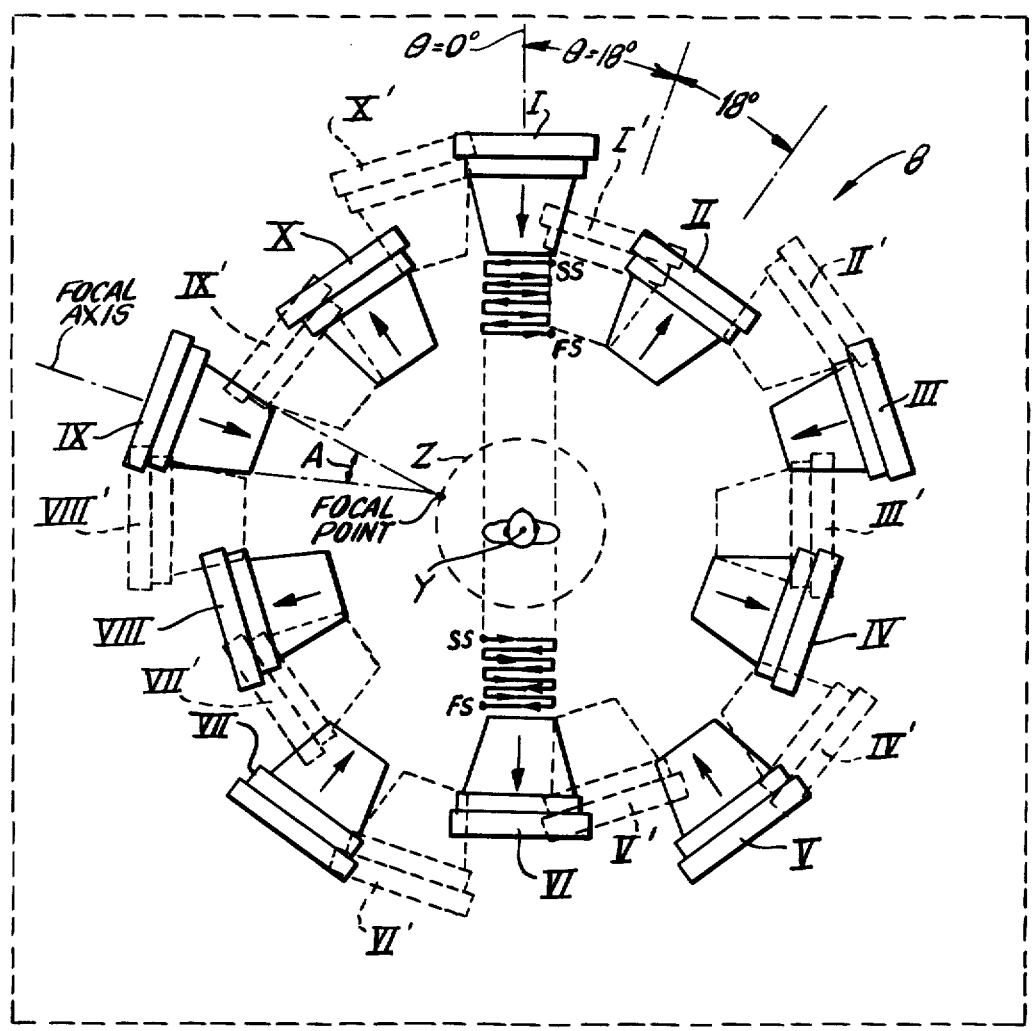
Figure 2A:
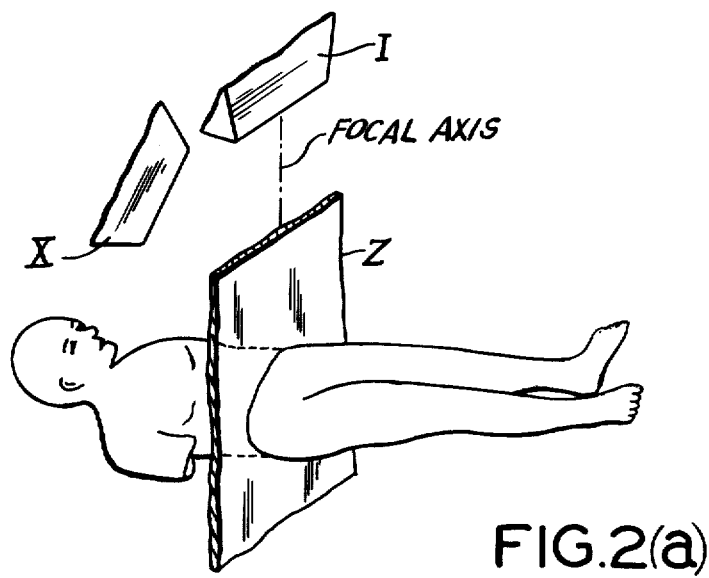
Figure 3:
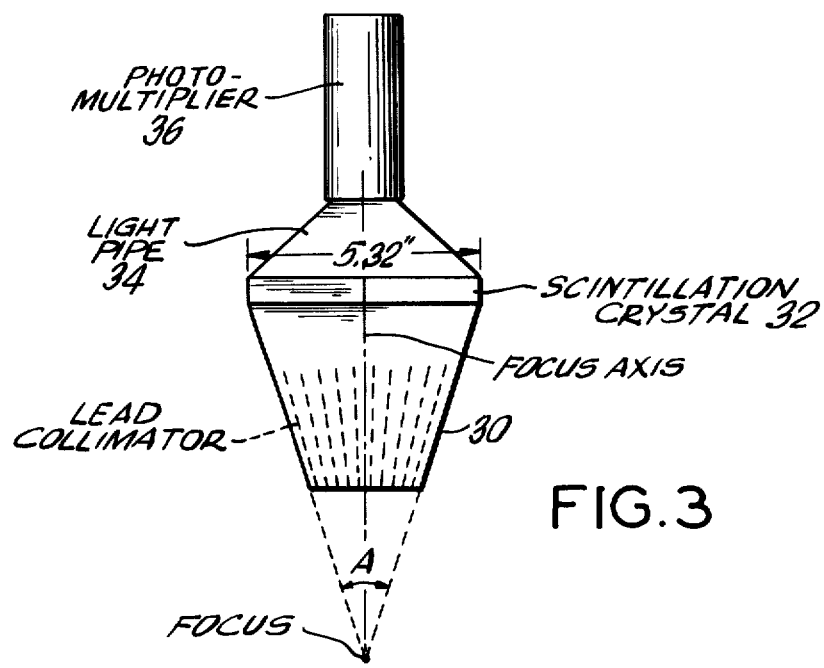
Figure 3A:
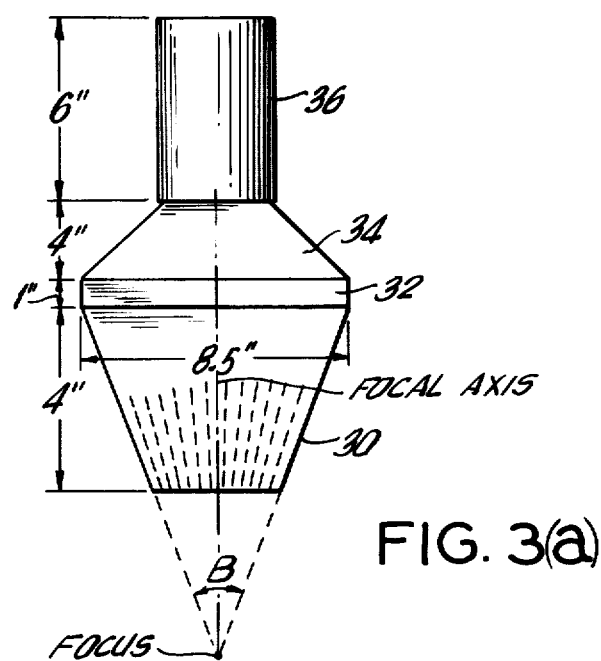
Figure 3B:
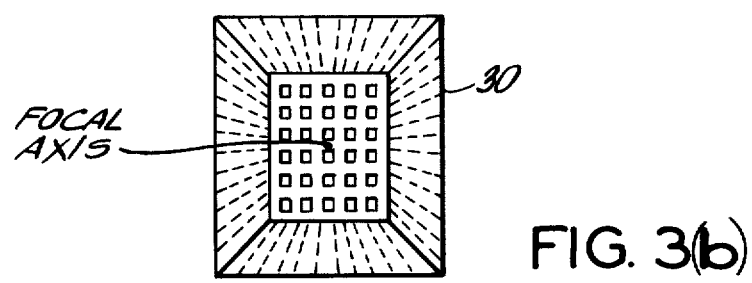
Figure 4A:
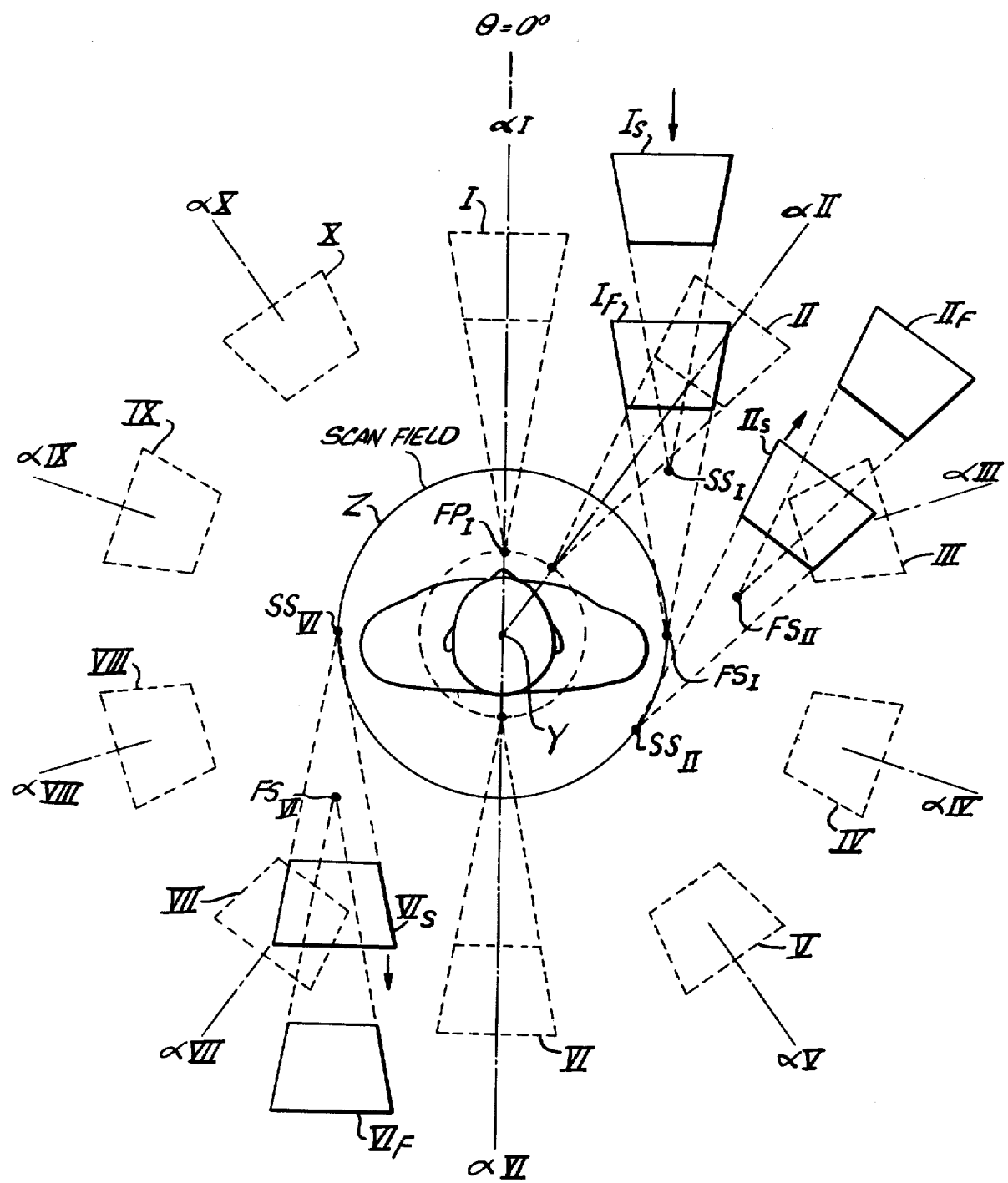
Figure 4B:
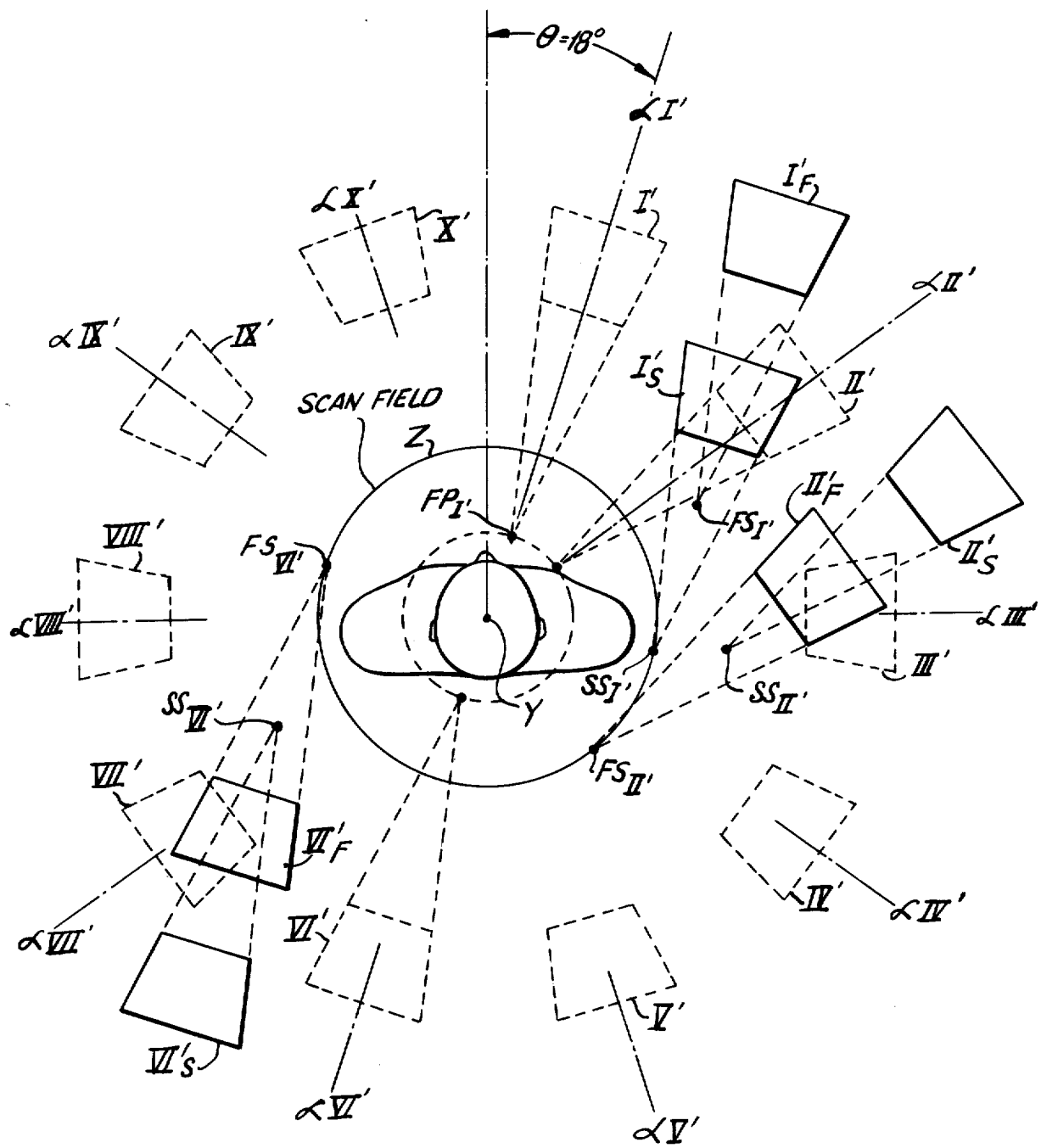
Figure 5:
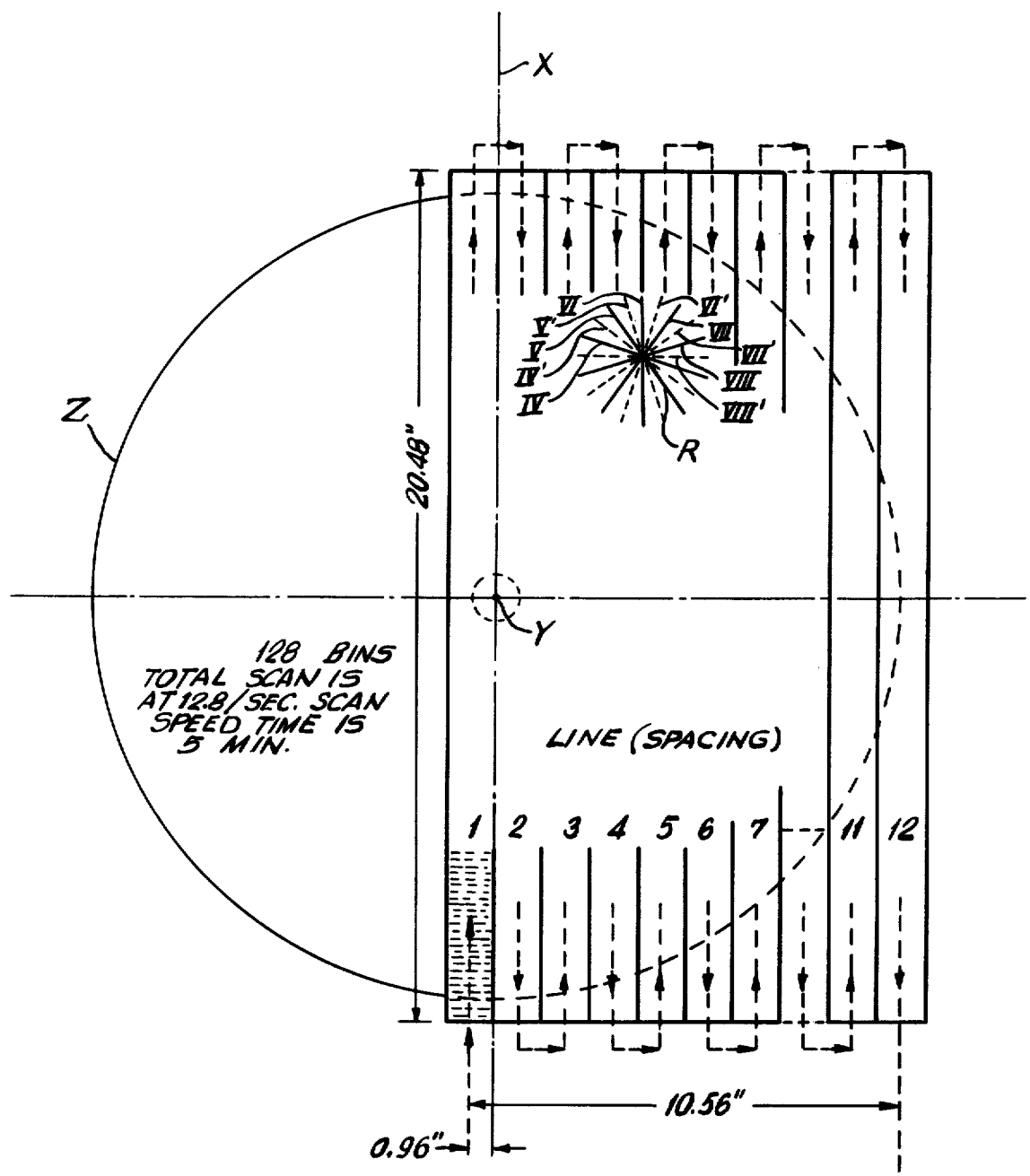
Figure 5A:
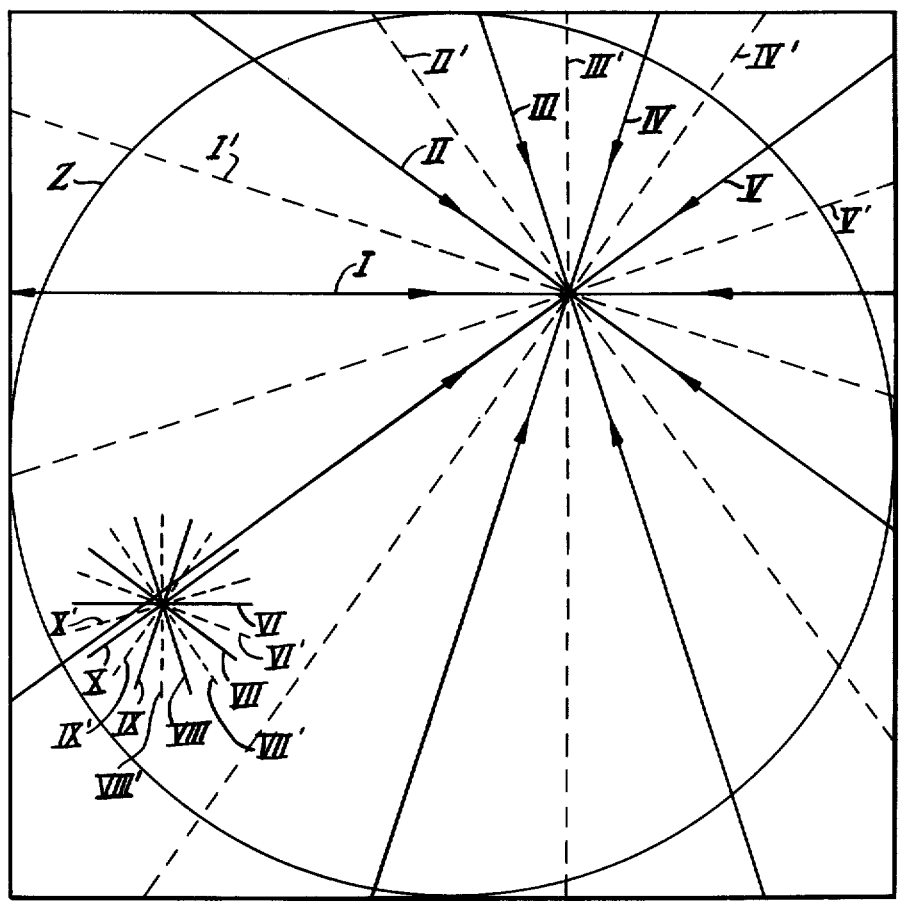
Figure 5B:
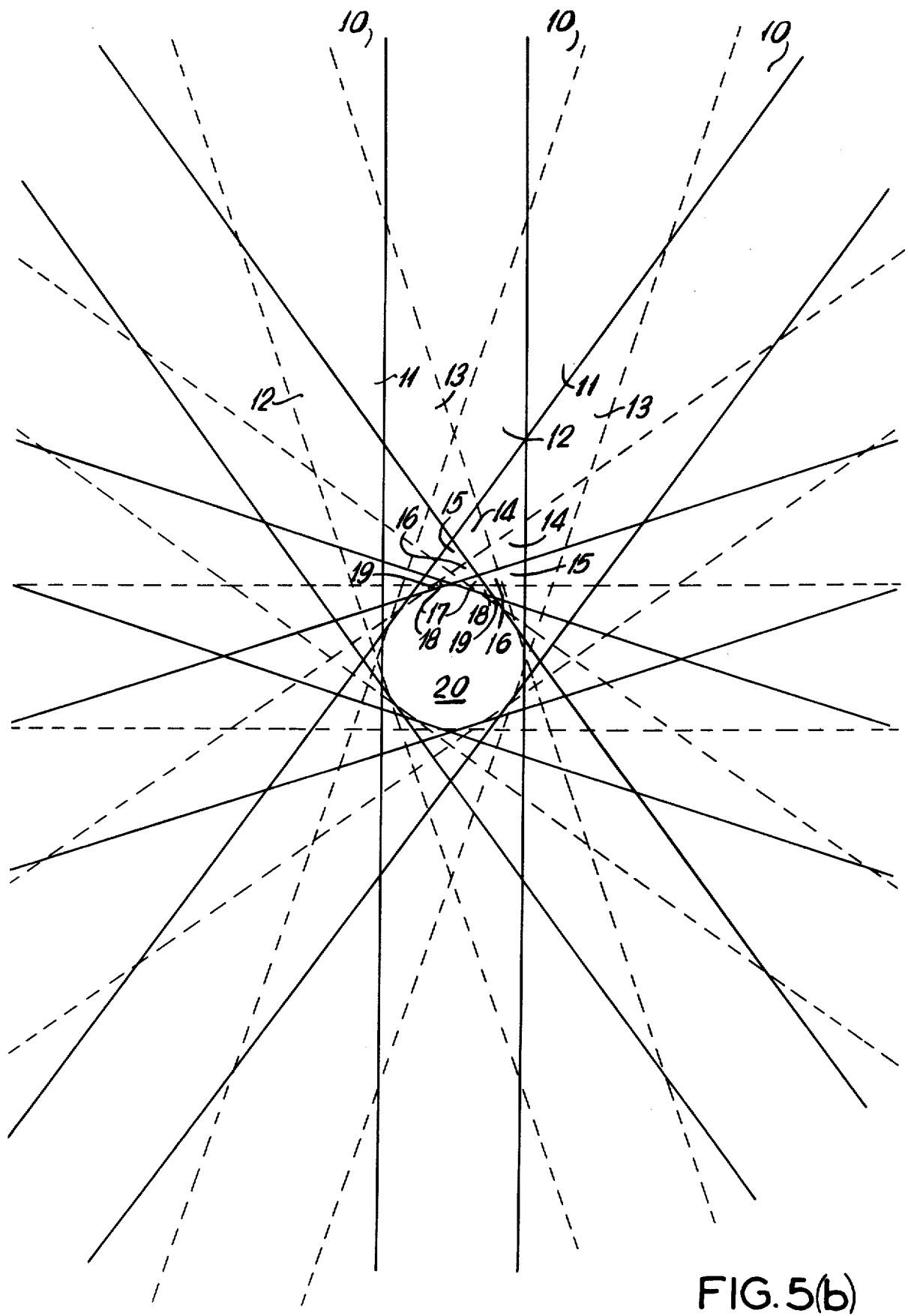

Other objects will be apparent from the following description and claims taken in conjunction with the drawing wherein FIG. 1 and 1(a) show the general arrangement of a particular embodiment of the present invention FIG. 2 shows, somewhat schematically, an imager in accordance with the present invention FIGS. 2(a), 2(b) and 2(c) illustrate a patient in relation to the imager of the present invention FIGS. 3, 3(a) and 3(b) show a detector arrangement, including a highly focused collimator, for use in connection with the present invention FIGS. 4(a) and 4(b) illustrate schematically an arrangement of highly focused collimators in accordance with the present invention and further illustrating representative relative movement of the collimators FIG. 4(c) and 4(d) illustrate schematically scanning patterns of highly focused collimators in accordance with the present invention FIG. 5 shows a preferred scanning pattern in accordance with the present invention FIGS. 5(a) and 5(b) illustrate particular representative portions of the scanning pattern of FIG. 5

Figure 6:
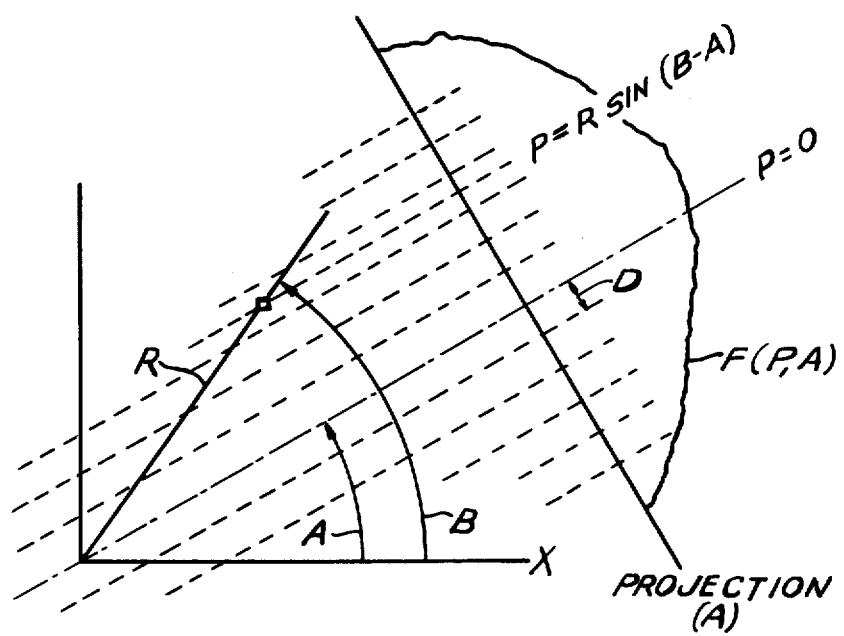
Figure 7:
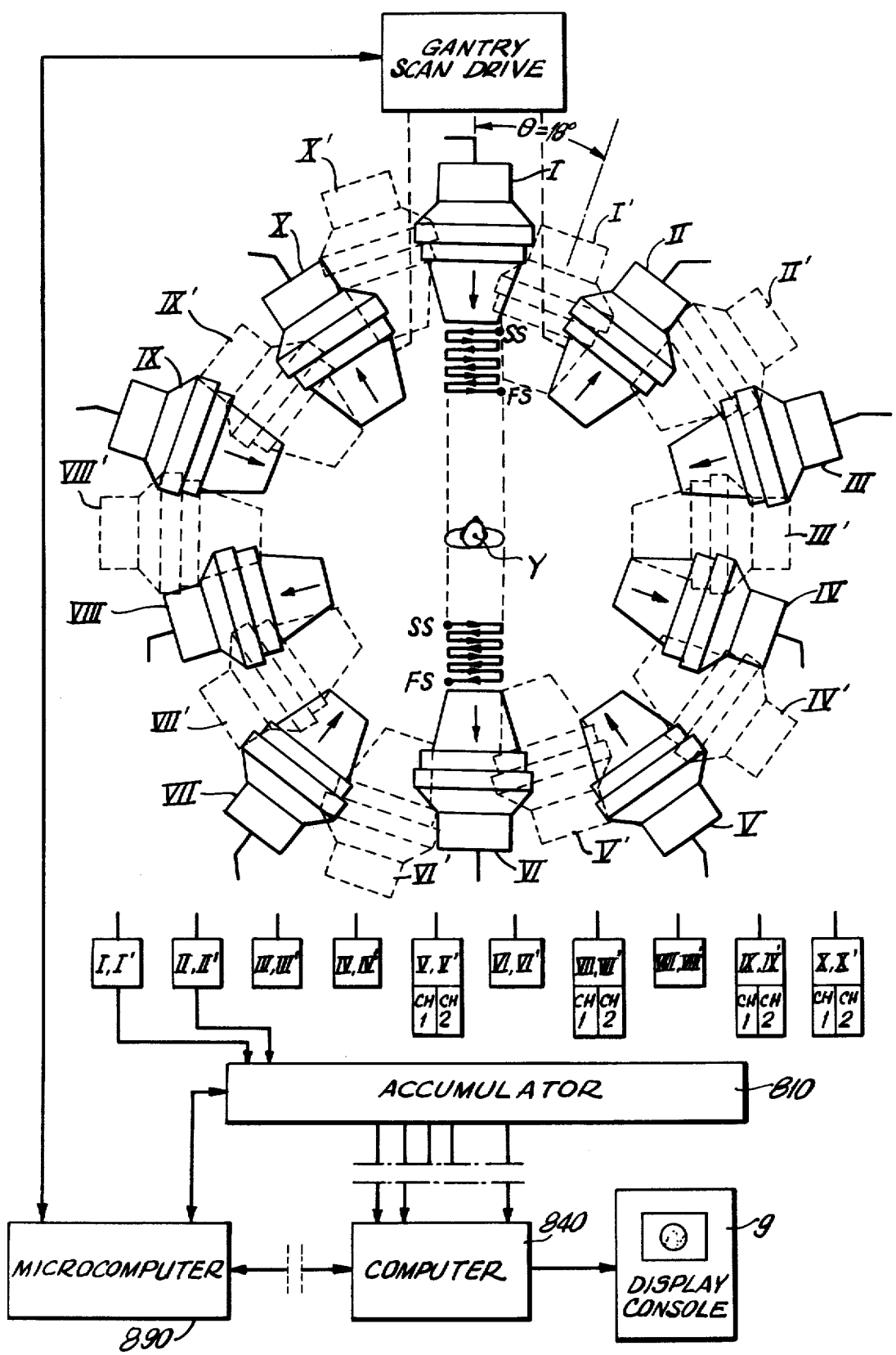
Figure 9B:
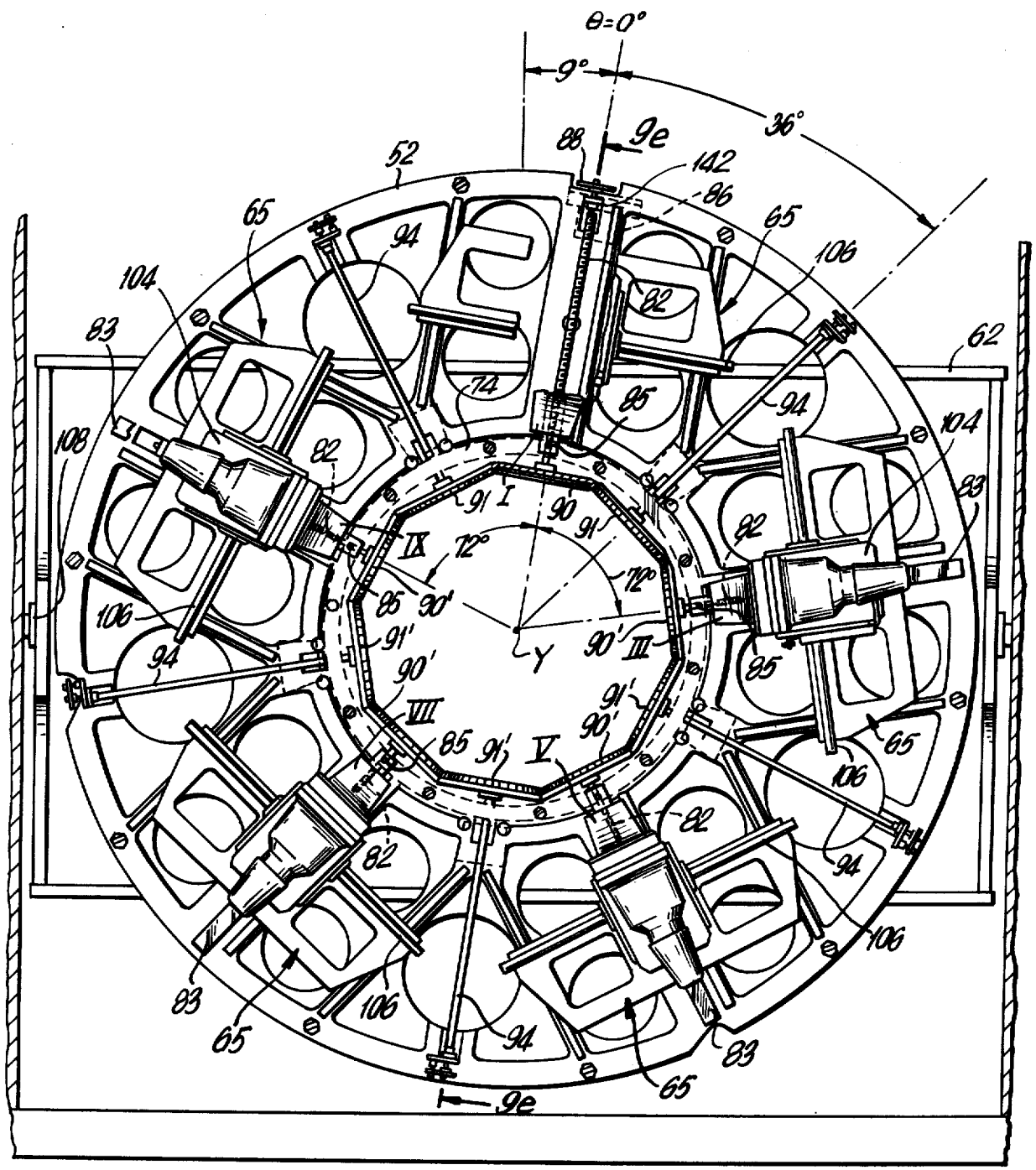
Figure 9C:
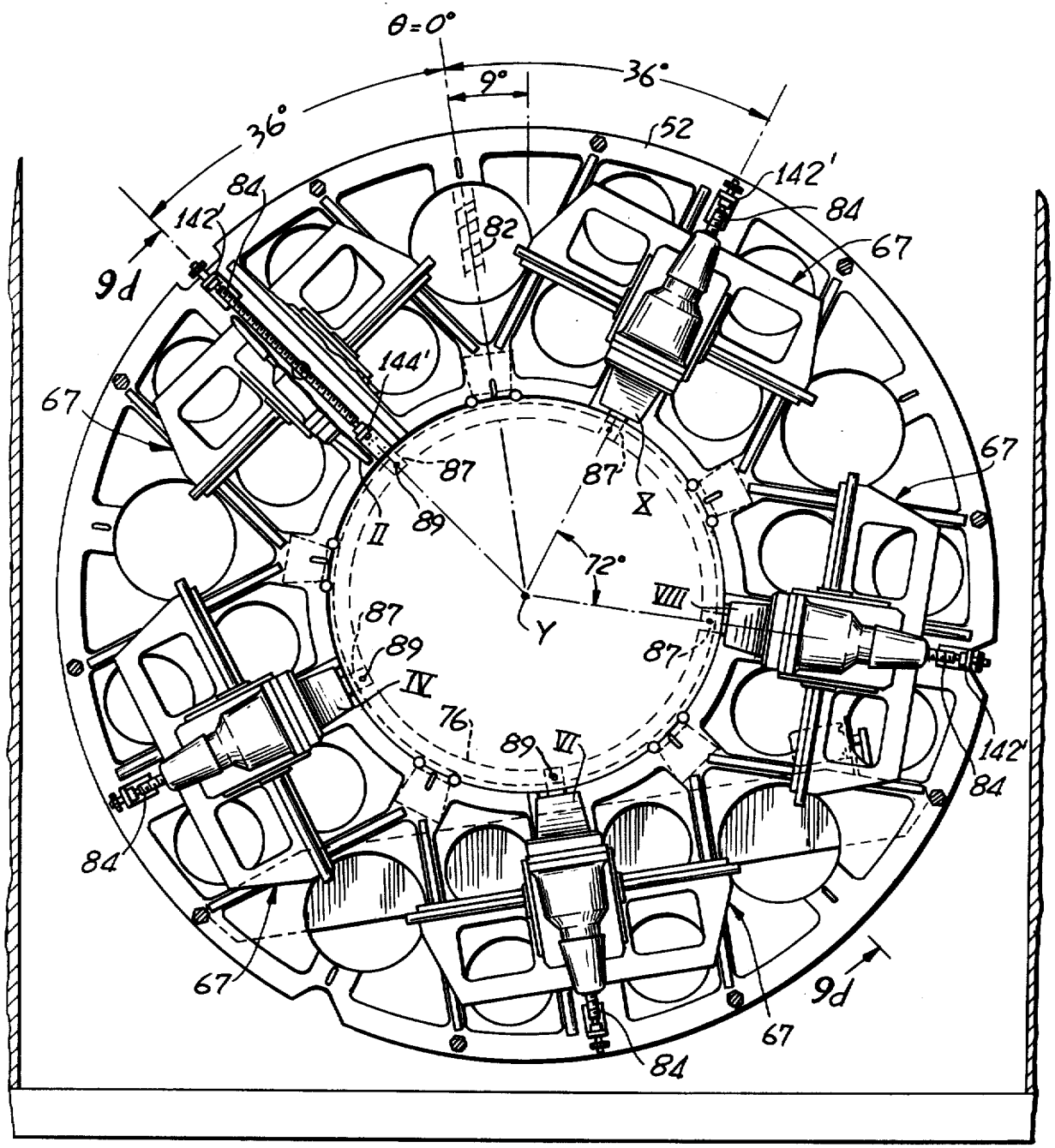
Figure 9D:
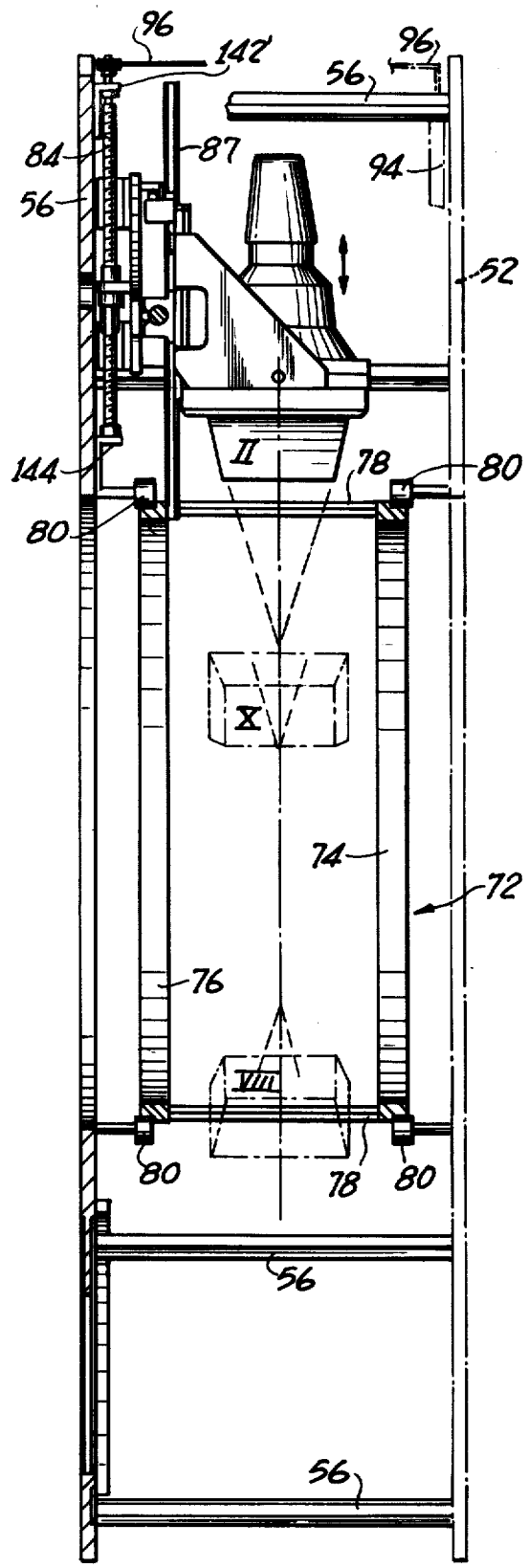
Figure 9E:
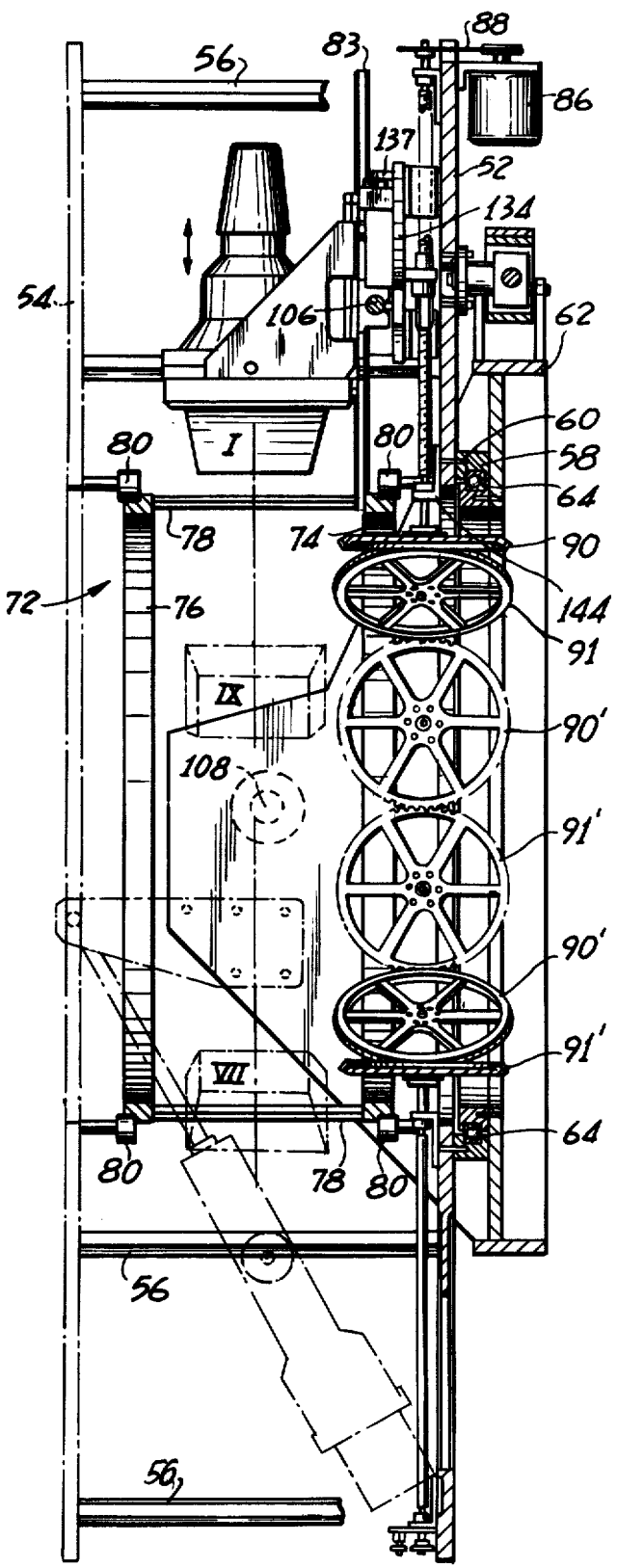
Figure 9I:
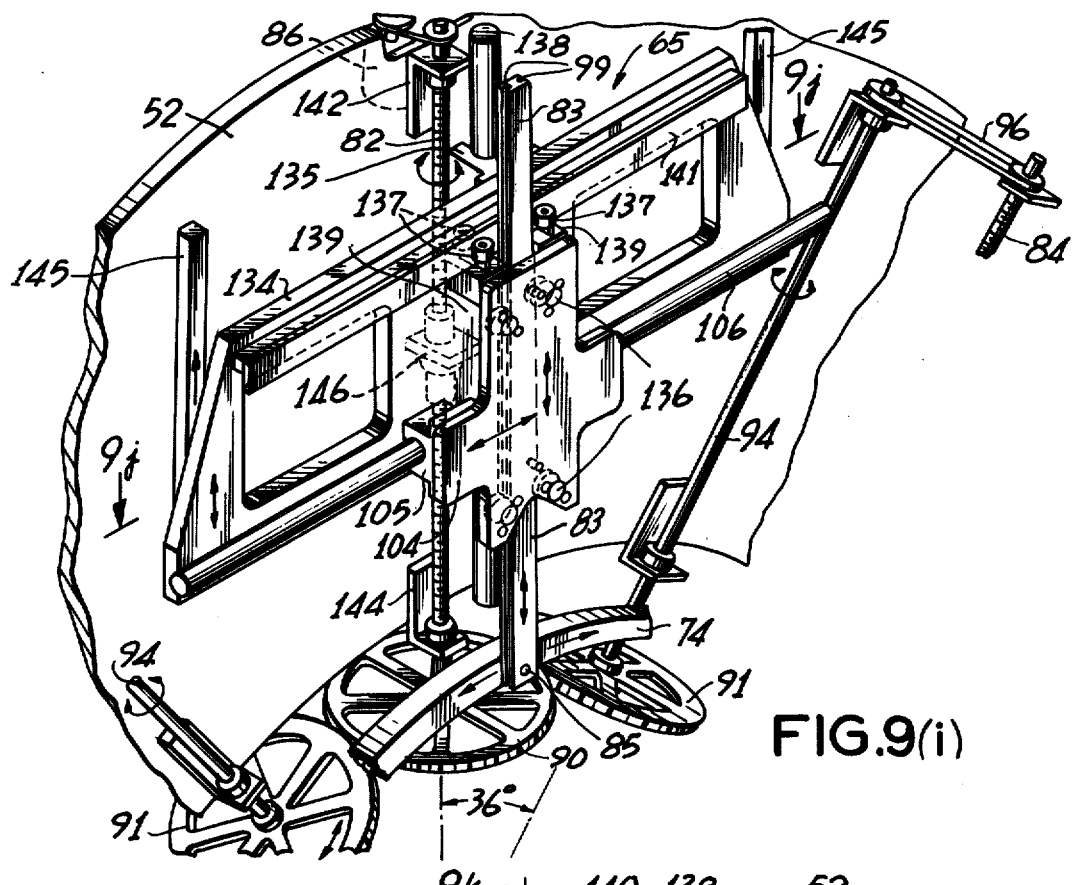
Figure 9J:
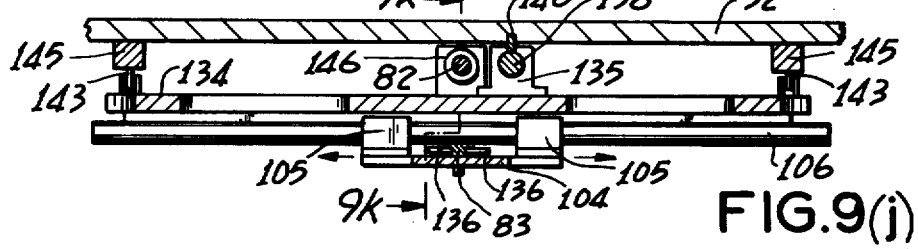
Figure 9K:
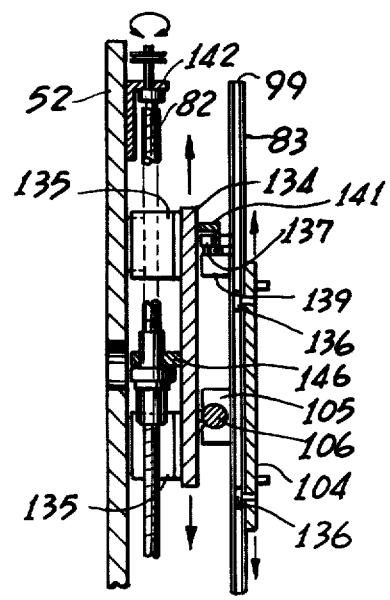
Figure 9M:
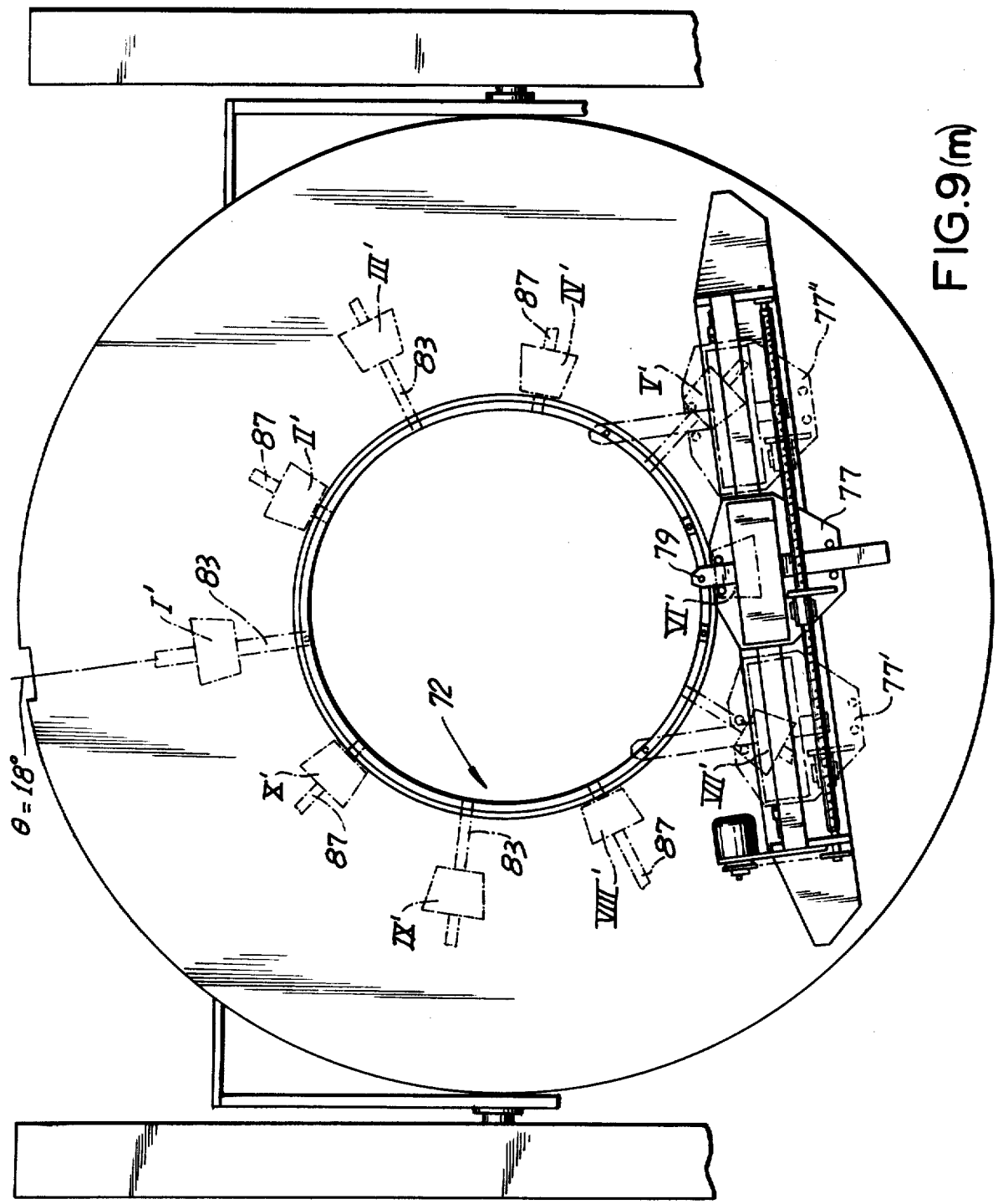
Figure 9N:
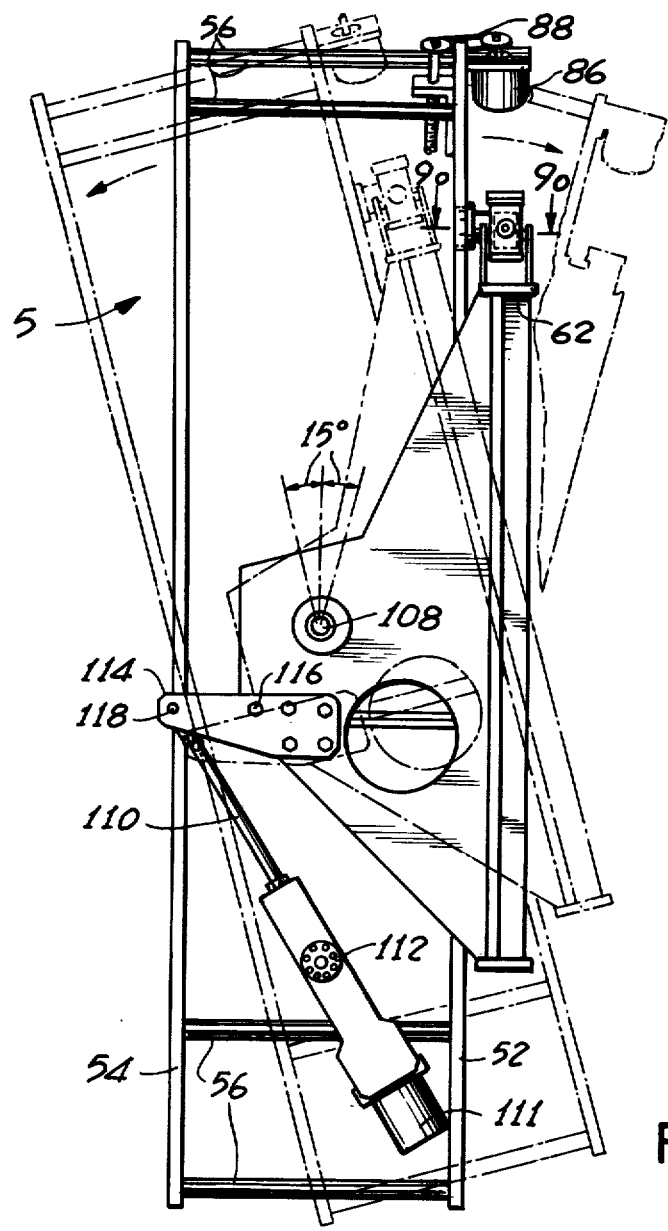
Figure 9O:
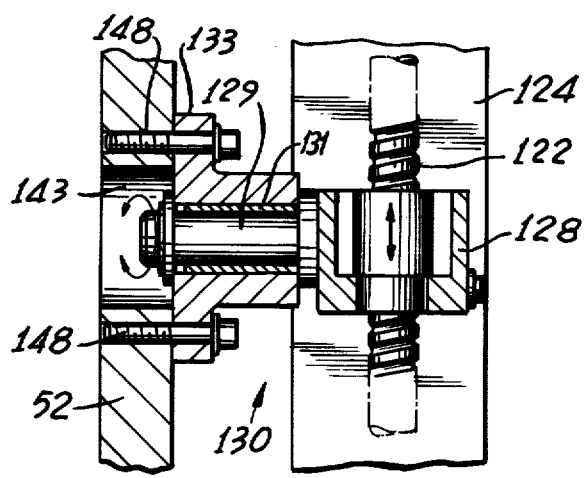
Figure 10A:
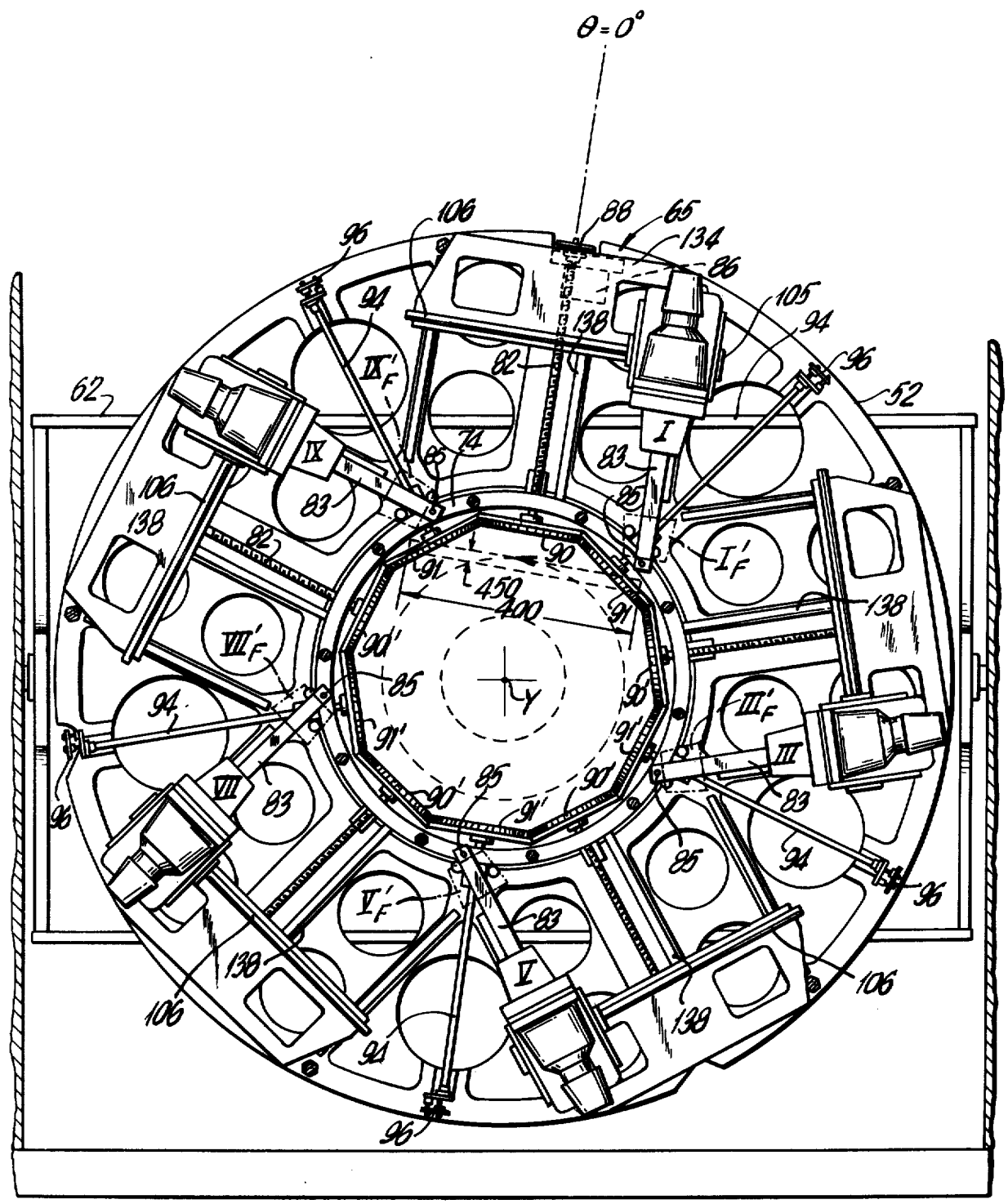
Figure 10B:
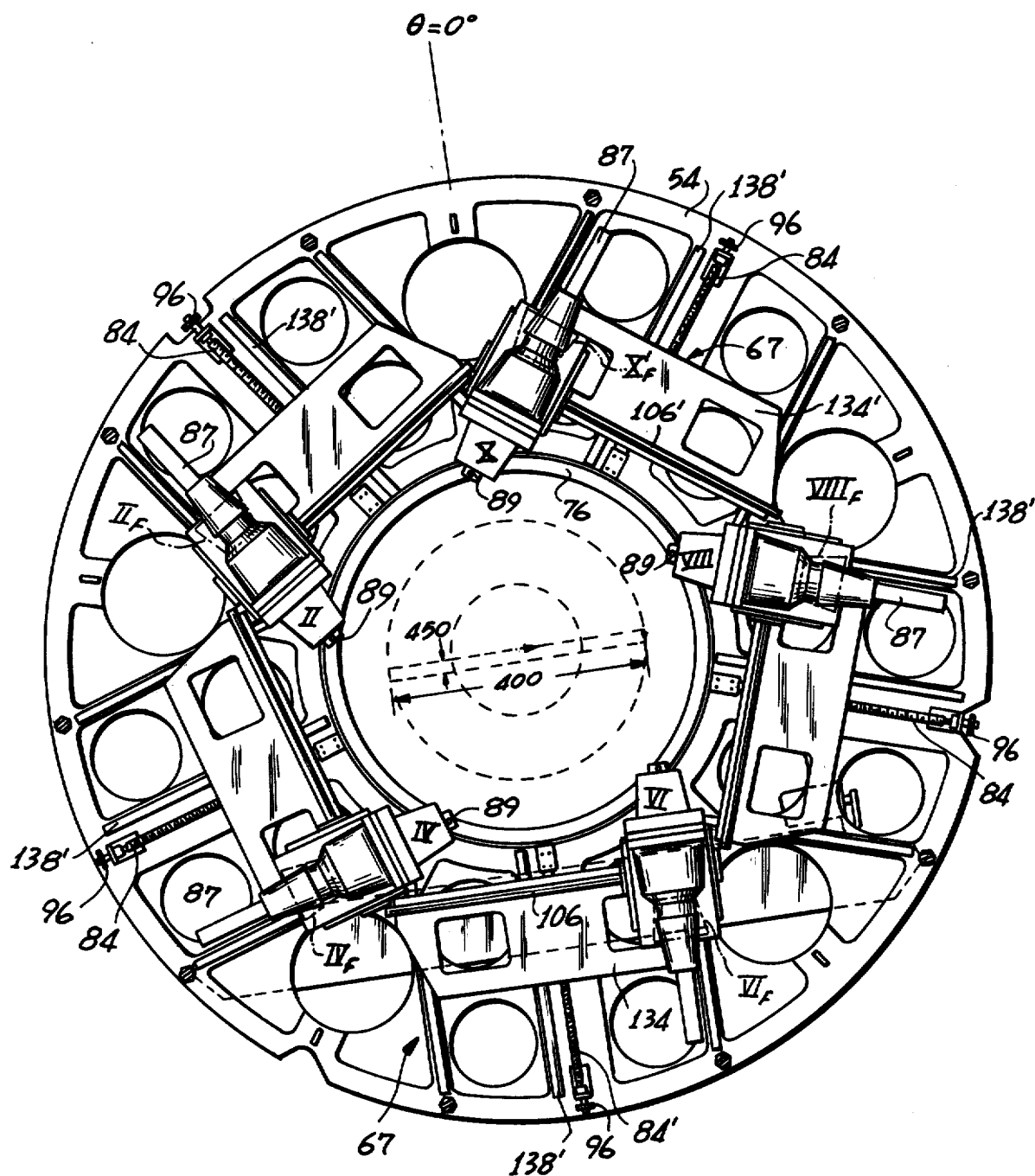
Figure 10C:
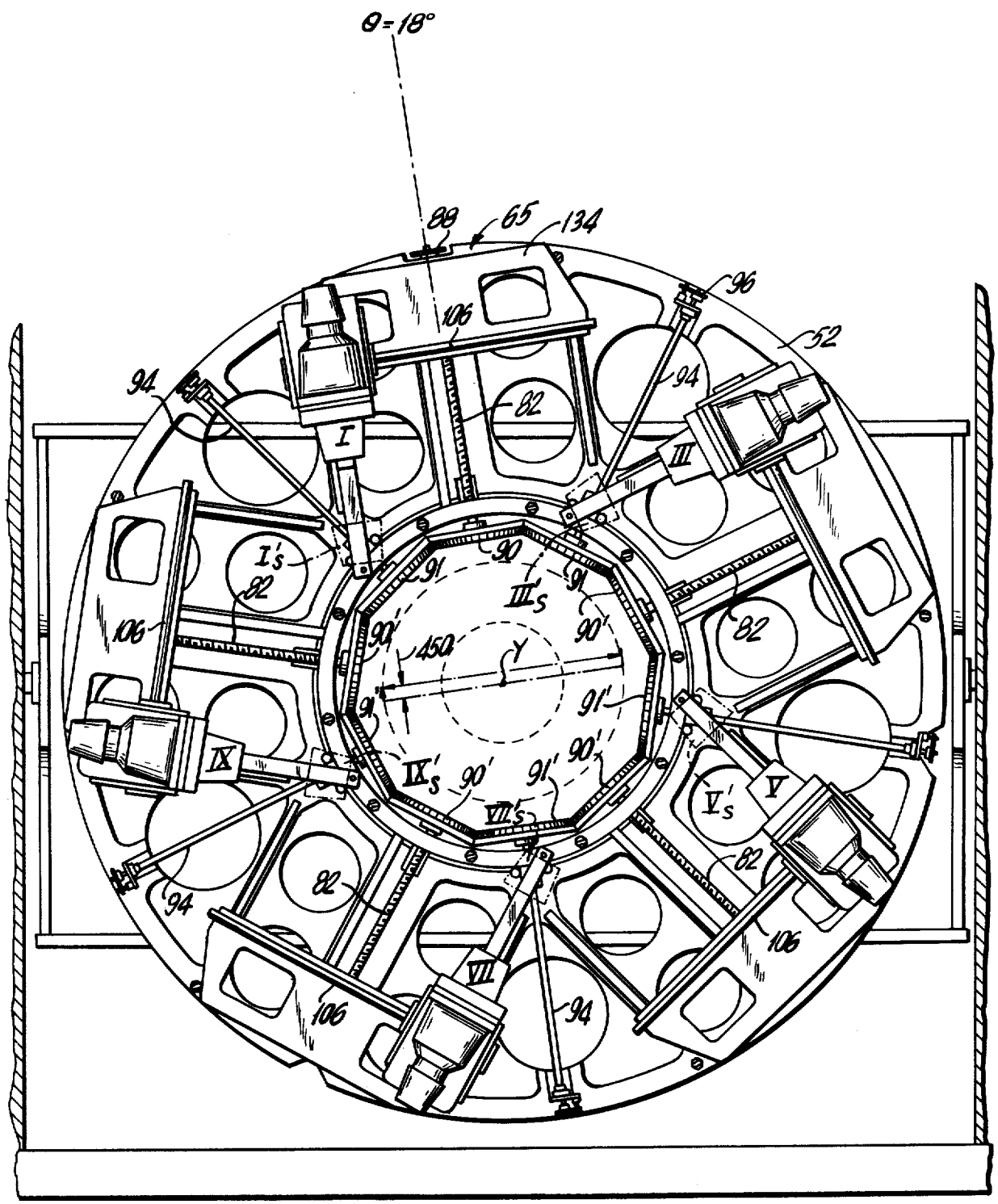
Figure 10D:
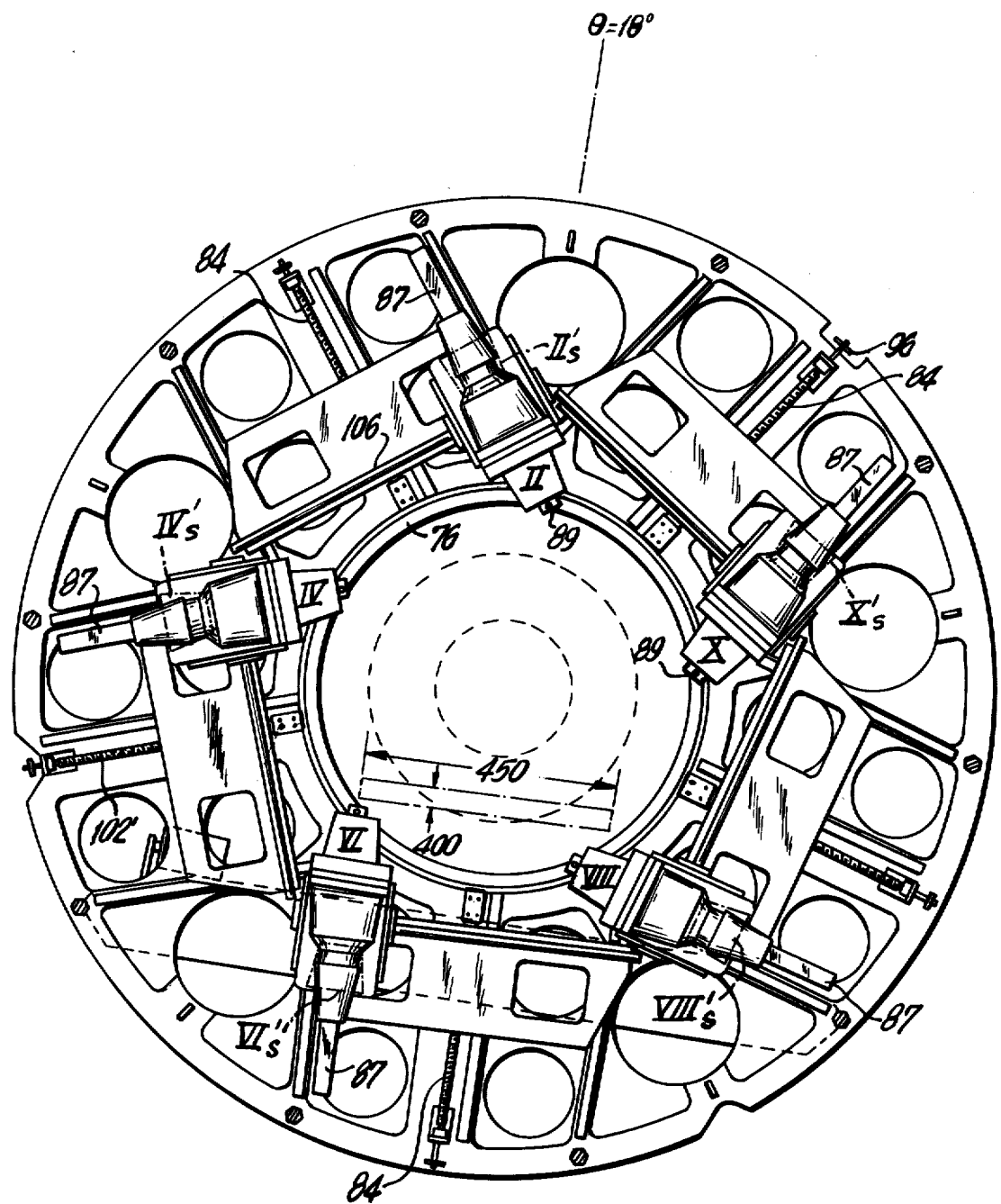
Figure 11:
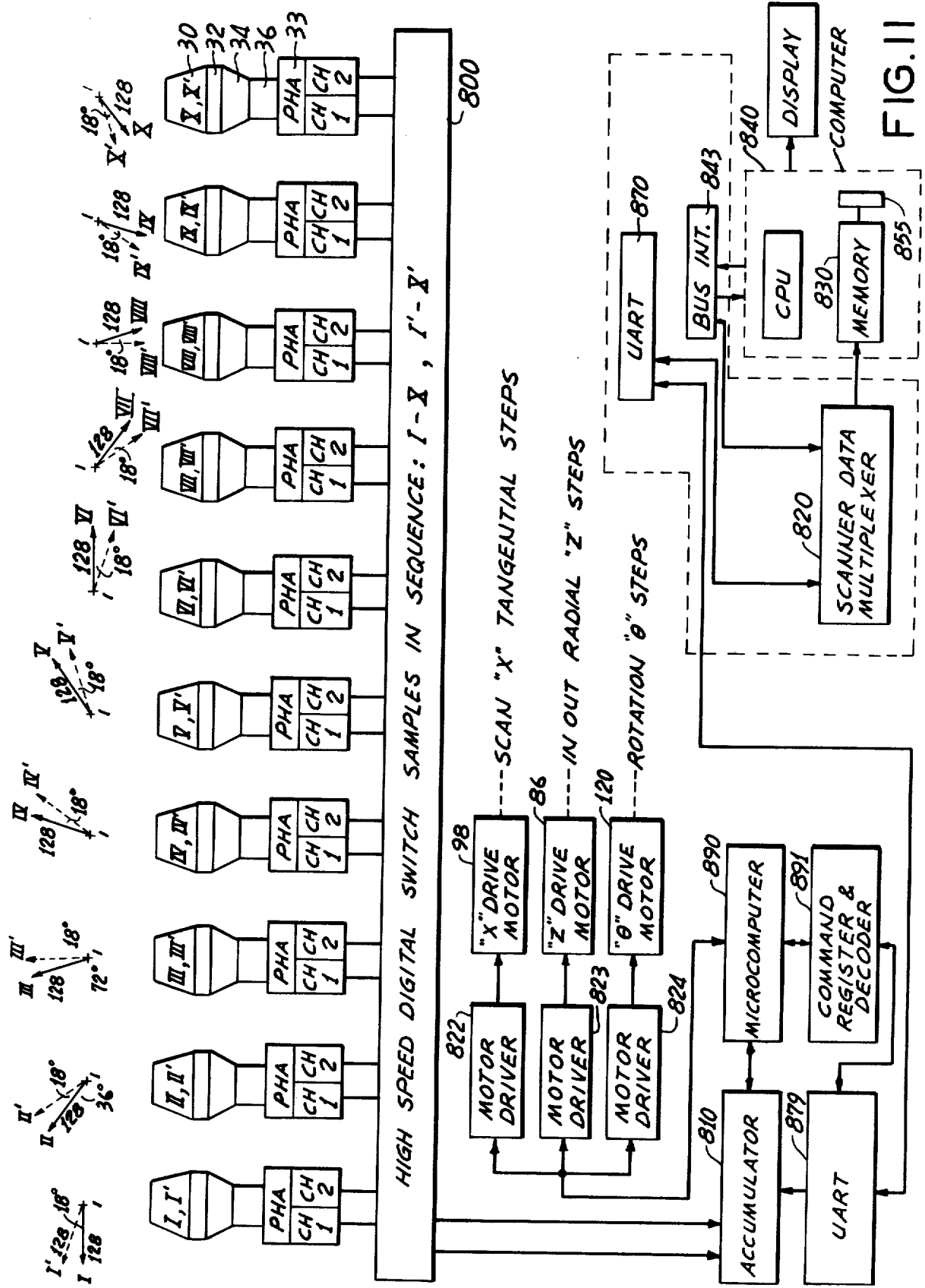
Figure 11A:
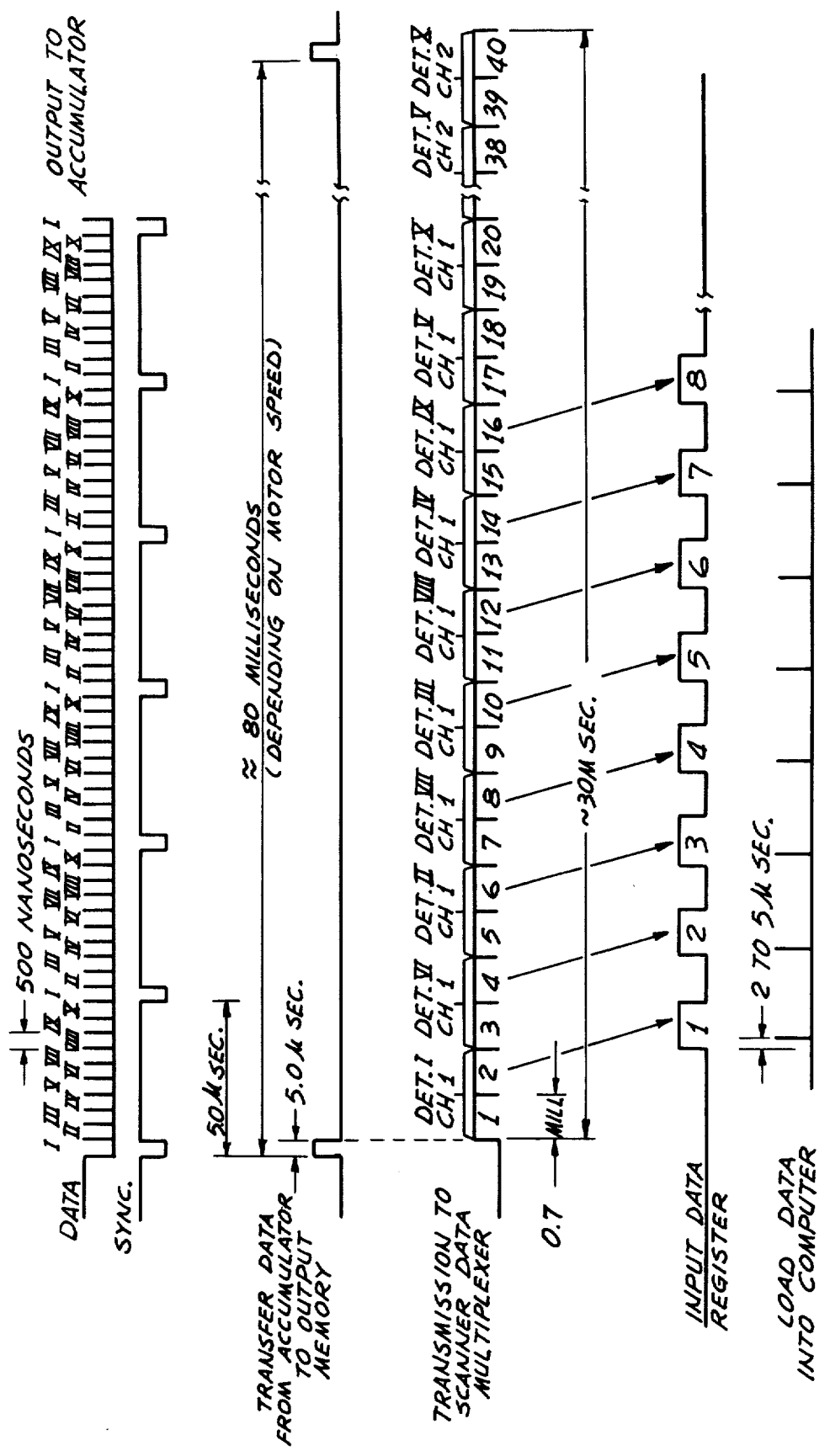
Figure 11B:
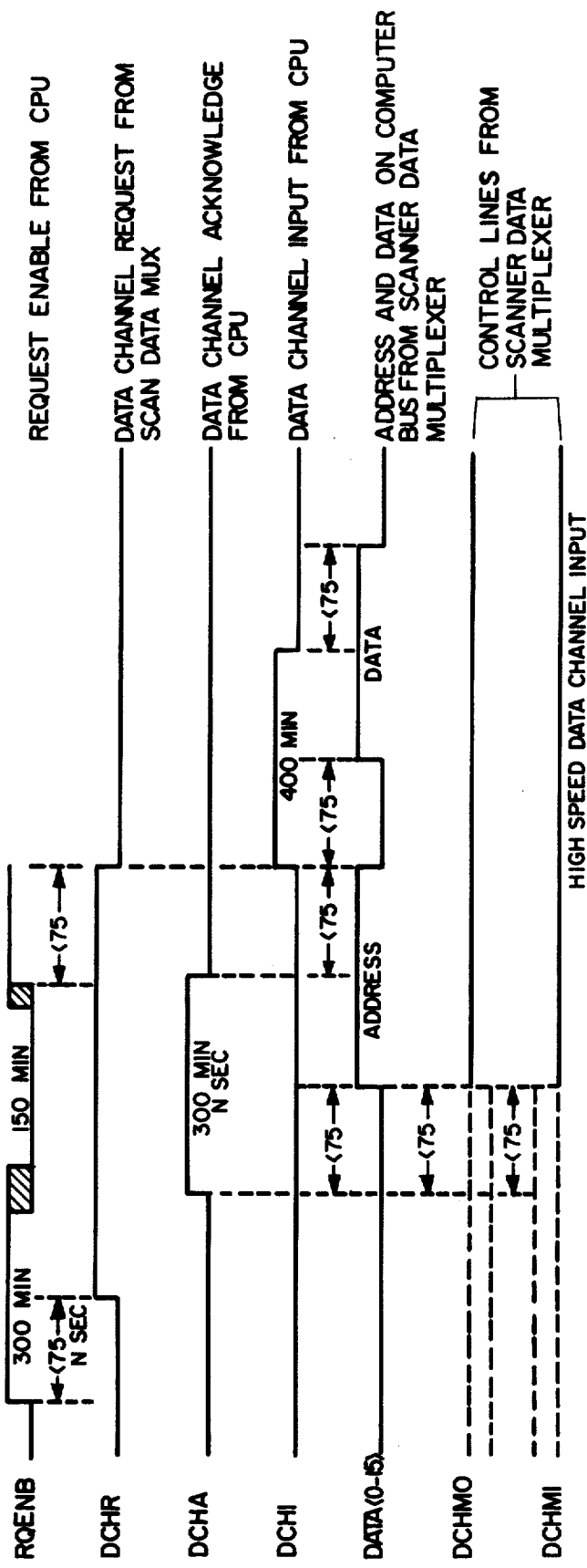
Figure 11C:
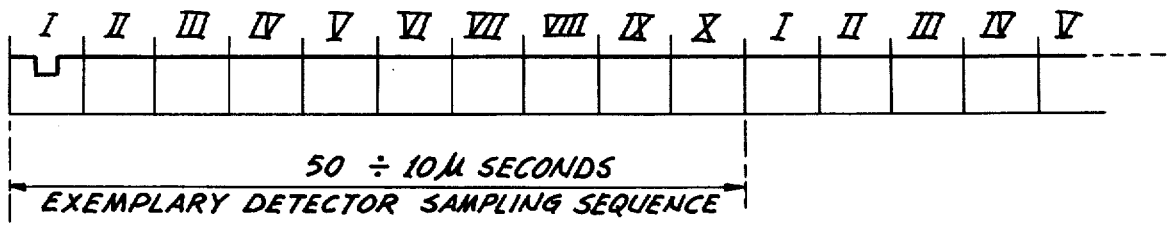

FIG. 6 is a diagram used in connection with a mathematical presentation in the specification FIG. 7 schematically represents a general arrangement for the imager of the present invention FIG. 8 shows a display provided through the use of the present invention FIGS. 9, 9(a)–9(o) and 10(a)–10(d) show various views of the preferred apparatus for the practice of the present invention FIG. 11 shows a general schematic for the transfer of data from the imager of the present invention to a general purpose computer FIGS. 11(a)–11(c) show timing diagrams related to FIG. 11

Figure 11E:
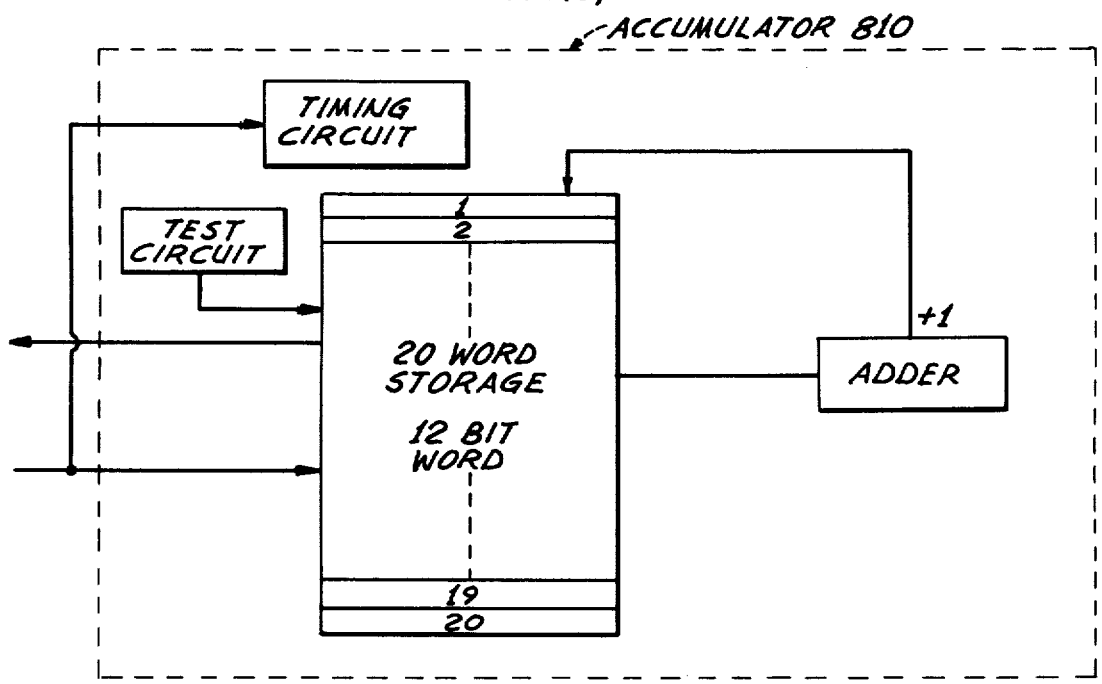
Figure 11F:
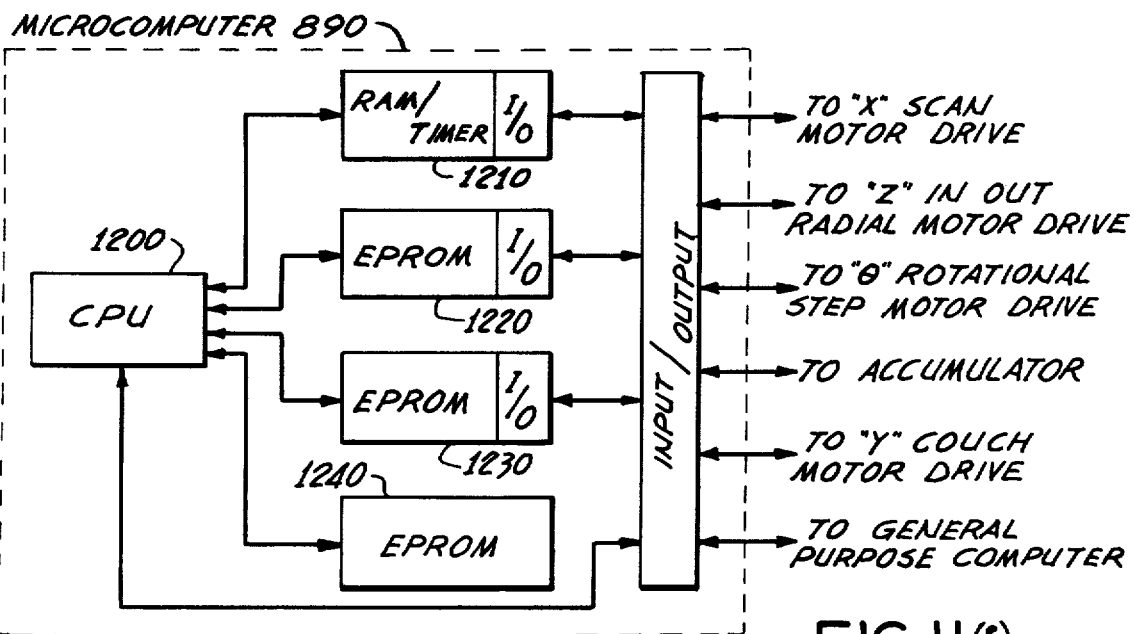
Figure 11D:
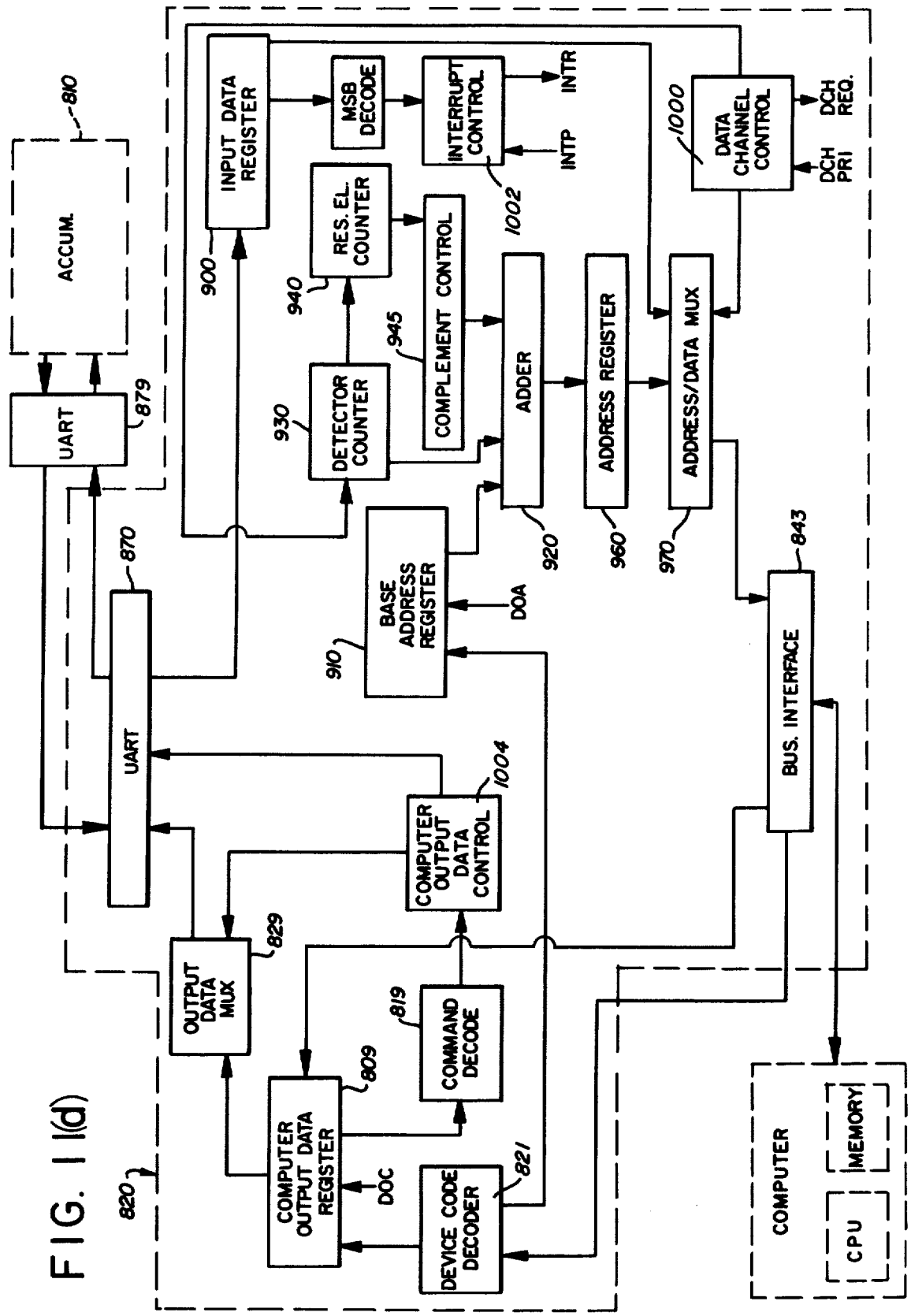

FIG. 11(d) shows a preferred embodiment of the scanner data multiplexer shown in FIG. 11

FIGS. 11(e) and 11(f) illustrate various components shown in FIGS. 11 to 11(d)

Figure 12:
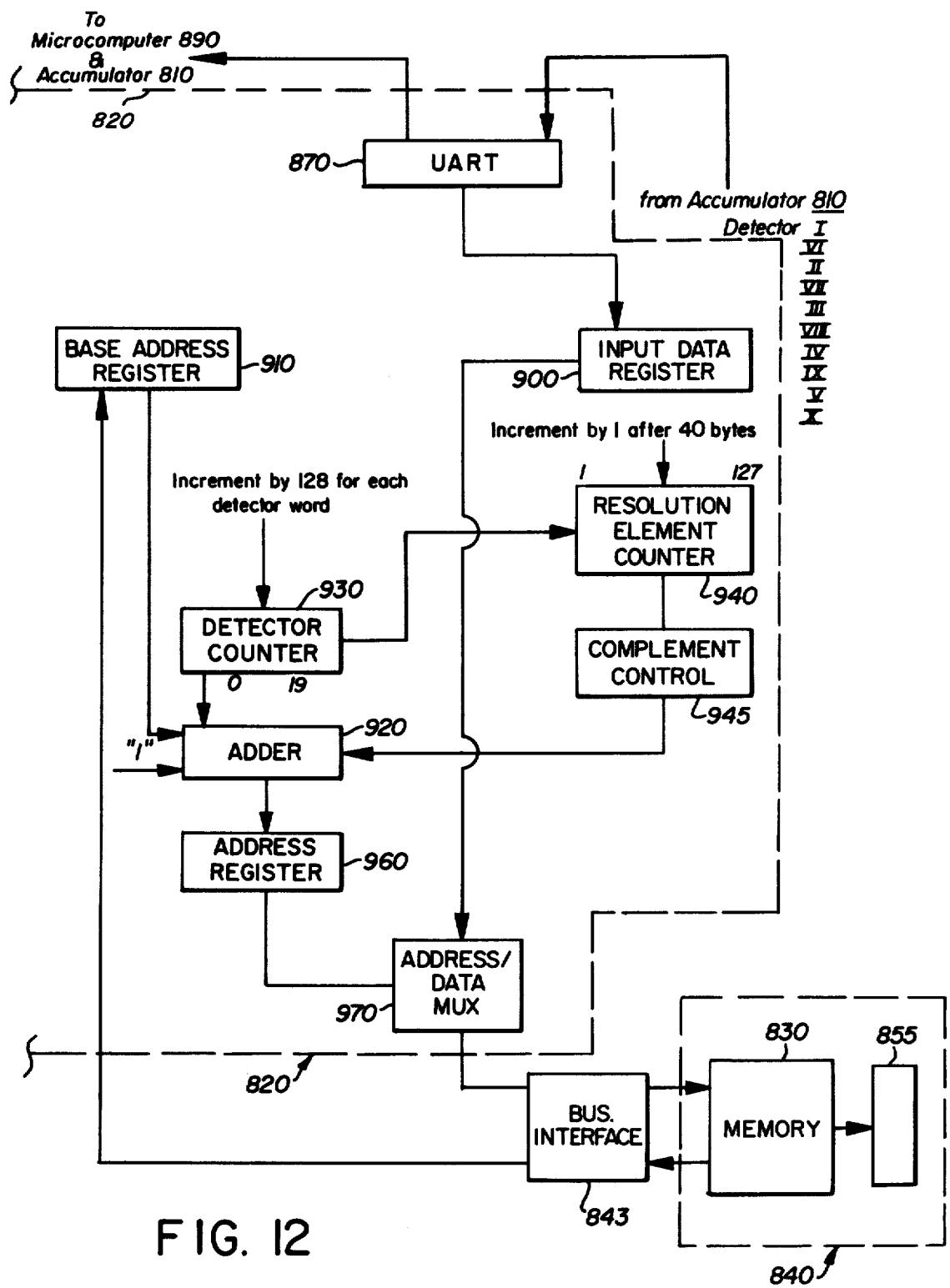

FIG. 12 schematically shows a portion of the device of FIG. 11(d)

Figure 13:
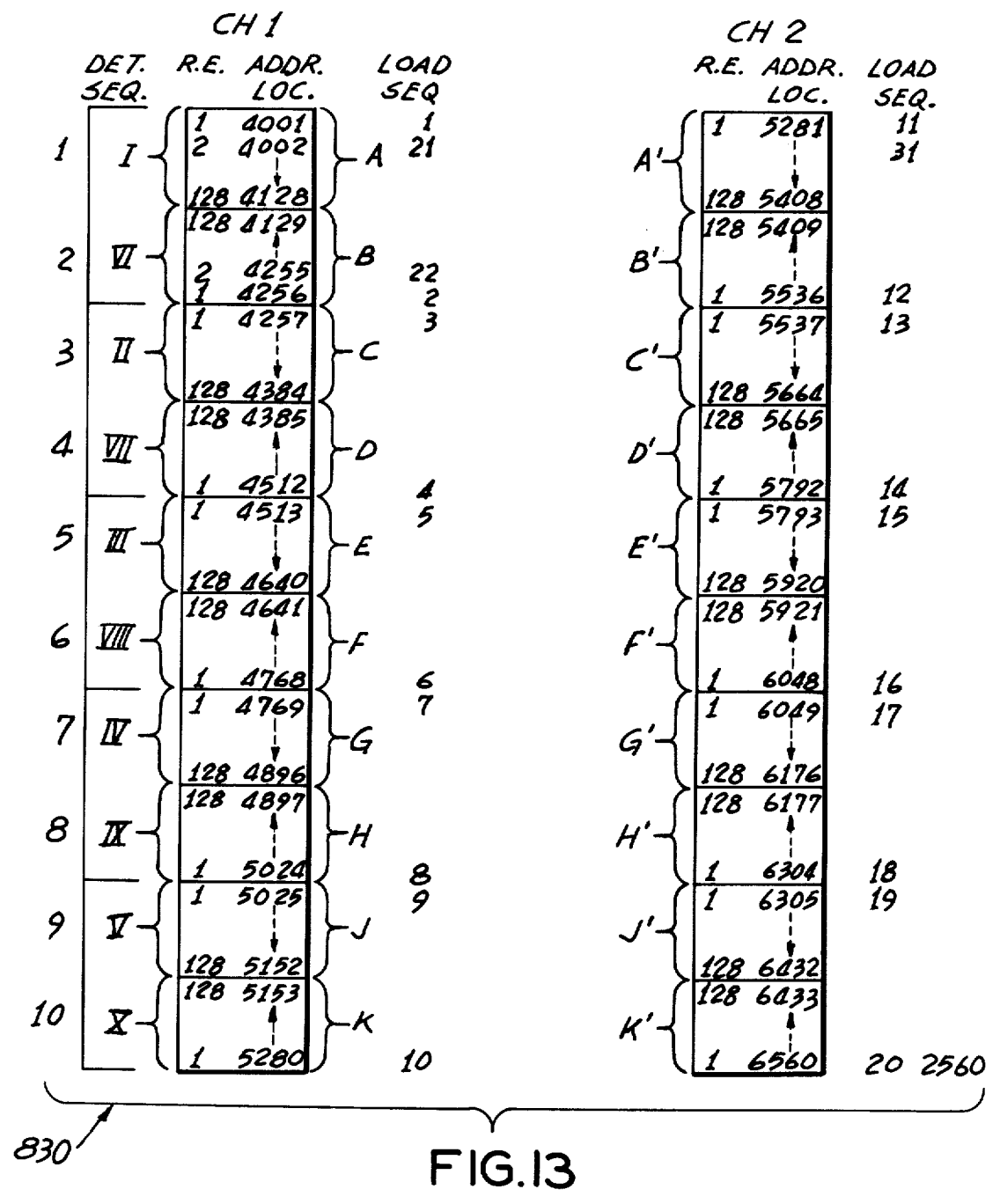
Figure 13A:
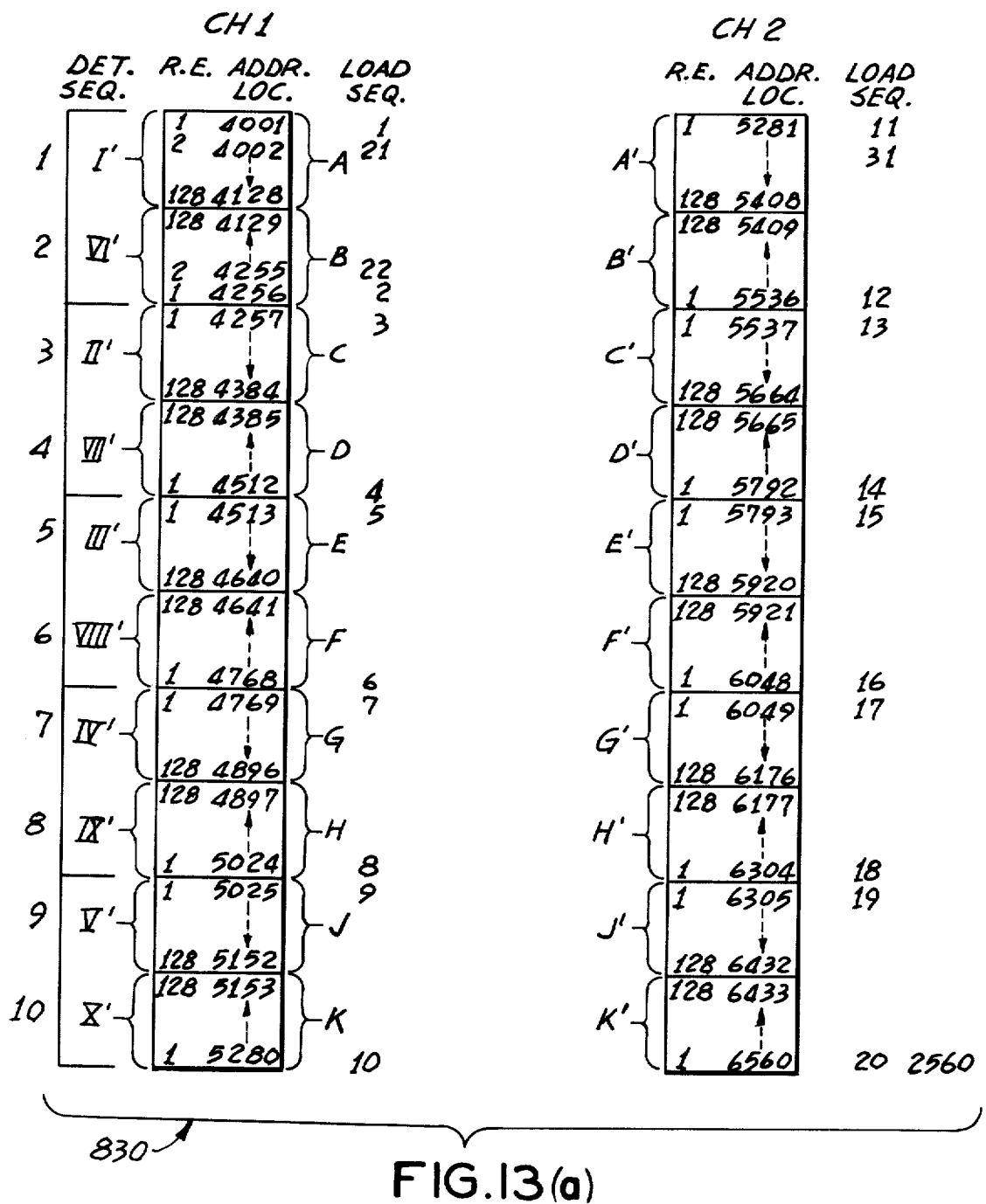

FIGS. 13 and 13(a) illustrate the loading of buffer storage in accordance with the device of FIG. 12

FIG. 14(a)–(d) shows command codes relevant to the device of FIG. 11(d).

With reference to FIG. 1, a patent's couch is indicated at 1 which is provided with controls, not shown, for raising and lowering the couch 1, and for moving the body rest 3, of couch 1, in and out of the opening 5 of the gantry indicated at 4. Within gantry 4, as hereinafter more fully described, there is arranged, in a unique and novel manner, a plurality of scanning detectors, having highly focused collimators, from which electrical signals are obtained which are readily processed, e.g. by a general purpose computer, and enable a display at console 9 of a transverse body section of an organ of a radionuclide administered patient, which display exhibits high sensitivity quantification and spatial resolution. The patient's couch 1 is moveable in and out of the opening 5 of the gantry 4 to provide for the scanning of a plurality of transverse body sections.

With reference to FIG. 2, this figure shows at 8 an essentially schematic representation of the arrangement of scanning detectors within gantry 4. Each of the detectors indicated at I to X in FIG. 2 is of a type more fully illustrated in FIGS. 3, 3(a); and 3(b) which show a highly focused lead collimator at 30, a scintillation crystal at 32, a light pipe at 34 and a photomultiplier tube at 36. Such an arrangement suitably has the dimensions shown in the drawing when ten detectors are used and suitably comprise a collimator made of antimony-bearing lead alloy containing a 26 × 30 array of tapered holes of rectangular cross-section. These holes are typically 0.13 × 0.19 inches on the face of the collimator and abuts the scintillation crystal 32, and about 60% of that size at the opposite face. All of the holes are convergent so that the axes intersect at a focus 13 inches from the collimator. The septa separating the holes are approximately 0.50 inch thick at at the crystal face. A typical design resolution of collimator 30, defined as the full width between two points that give half amplitude for a point source of radiation is 0.6 inch in the plane of the transverse section and 0.6 inch perpendicular to the slice (slice thickness).

The scintillation crystal 32 typically comprises a thallium activated sodium iodide crystal mounted within a rectangular aluminum box and sealed under a window of ultraviolet transmitting glass. The bottom wall of the aluminum housing is thin, preferably less than 0.020 inches, to minimize absorption and scattering of the incident gamma rays.

A very important feature of the present invention is that the collimator used is highly focused at a single focal point, i.e. all the holes in the collimator converge at the focal point so that the collimator includes a large solid angle from about 0.03 to 0.6 steradian, preferably about 0.12 steradian, for collecting radiation.

In a configuration such as illustrated schematically in FIG. 2, where ten focused collimators are used, the angle "A" is approximately and as close as practical to 36° (360÷10), e.g. about 33° and the angle "B" (FIG. 3(a)) is about 24°. When other than ten collimators are used, e.g., 4, 8, 12, the design for angle "A" is (±20%) obtained by dividing the number of collimators into 360°. In the present invention, the focal length of the collimators, e.g., (13 inches) is somewhat more than one-half the diameter of the scan field which surrounds the portion of the patients body which is scanned.

In the present invention, the preferred number of collimators is ten to obtain high sensitivity and resolution in a short period of time, e.g., about 5 minutes per slice. The preferred range for the number of collimators is from 4 to 40 even numbers of collimators. Even numbers of collimators are preferred since they can be arranged in pairs with each collimator scanning half of the transverse section of the organ thereby minimizing effects of attenuation and scattering. With odd numbers of collimators, each collimator preferably scans the entire transverse section of the organ.

Referring again to FIG. 2, detectors I to X are mechanically mounted and coupled in gantry 4, as hereinafter more fully described, to provide focal point scanning of a transverse section "Z" which is normal to the head-to-toe axis of the patient and indicated schematically in FIG. 2(a). With reference to FIG. 2, which shows exemplary distances, the position of the equi-angularly displaced detectors I-X can be considered to represent the start (or finish) of the first half of a focal point scan in accordance with the present invention. The adjacent detectors are shown alternately in what can be called "full out" and "full in" positions. Upon commencement of a scan, each detector I-X moves in a straight line tangential to the scan field Z in the same rotational sense (either clockwise or counter-clockwise angular rotation about the "head-to-toe" axis Y of the patient) the tangential travel of each detector being the same, a full diameter, or across two adjacent quadrants of scan field. Upon completion of each tangential travel, the initially "full in" detectors II, IV, VI, VIII and X move away from the axis Y a predetermined increment normal to the tangential travel, the initially "full out" detectors I, III, V, VII and IX move toward the axis Y by the same increment, and the direction of a tangential travel of all detectors is reversed. This coordinated movement of the detectors is repeated until the focal point of each detector scans at least one-half of the area of the scan field, preferably more than one-half as hereinafter described, at which time the first half of the scanning is completed and the initially "full in" detectors are in a "full out" position and vice versa. At this time, the entire array of detectors I-X is rotated 18° (360°÷10)÷2 to the positions I'-X' as shown in dotted lines in FIG. 2 and the above-described scanning operation is repeated to complete the second half of the scan, the previously "full in" detectors being "full out" detectors for the second half of the scan and vice versa. By the angular rotation of each detector an increment equal to one-half the angular displacement between detectors and repeating the scanning operation, the complete scan achieved is as if double the number of detectors were employed. That is with ten detectors, and an array rotation of $\theta = 18°$, the full scan obtained is the same as if twenty detectors were used. Consequently, a minimum number of highly focused collimators of quite short focal length can be used in the present invention to enable optimum collection of patient emitted radiation. While each detector in the present invention is required to "scan twice", about 4 minutes total, whereas using double the number of detectors would require each detector to "scan once" the required size of the scanning mechanism for double the number of detectors would be undesirably greatly increased as would the focal lengths and distance of the detectors from the scan field. It is to be noted that the region scanned by the focal point of each detector overlaps, by an angular segment, the focal point scan of other detectors. In the case of ten detectors, there is a 36° segment overlap (18° for an effective twenty detectors) of adjacent detectors and each scanned point in the scan field is effectively scanned by the focal point of at least ten detectors as hereinafter described.

By way of further explanation, FIG. 4(a) shows schematically in dotted lines, the detectors I-X at their respective halfway positions during the "first half of a scan. At the illustrative "½ way" positions of the "first half" of a scan shown in FIG. 4(a) all of the detectors I-X are at the same distance from axis Y and as particularly illustrated for detector I, the focal point $FP_1$ is halfway in the scan field. As the "first half" of the scan is completed, detector I moves from the position $I_{SS}$ (SS, Start-Scan I) in and over following the tangential and incremental motion previously described, to the position $I_F$ where the "first half" of the focal point scan for detector I is completed $FS_I$ (Full Scan I). Concurrently, the same relative motion is being experienced by detectors III, V, VII and IX. The relative movement of the even numbered detectors is represented by detector II. As the "first half" of the scan is completed, detector II moves from the position $II_S$ out and over to the position $II_F$ where the "first half" of the focal point scan for detector II is completed $FS_{II}$ (Full Scan II). FIG. 4(c) illustrates schematically the focal point scan provided by each of the six "inward" moving detectors I, III, V, VII and IX. The scan shown is provided, for the respective detector, along the respective radial angle indicated, i.e. $\alpha_I$, $\alpha_{III}$—$\alpha_{IX}$. A similar presentation is shown in FIG. 4(d) for the six "outward" going detectors II—X. Upon completion of the "first half" of the scan, detectors I-X are rotated 18° as hereinabove described for continuation of the "second half" of the scan. FIG. 4(b) shows detectors I-X after rotation 18° clockwise and identified in this position as I'-X' as in FIG. 2. As can be seen from FIGS. 4(a) and 4(b) the position $I_F$, after a rotation, $\theta$, of 18°, becomes $I'_S$, $II_F$ becomes $II'_S$, etc. FIG. 4(b) shows schematically, the detectors I'X' at their respective halfway positions during the "second half" of a scan. At the illustrative "½ way" positions of the "second half" of a scan shown in FIG. 4(b) all of the detectors I'-X' are at the same distance from the axis Y and as particularly illustrated for detector I', the focal point FP'$_I'$ is halfway in the scan field. As the "second half" of the scan is completed, detector I' moves from the position I'$_S$ out and over following the tangential and incremental motion previously described, to the position I'$_F$ where the "second half" of the focal point scan for detector I' is completed FS$_I'$ (Full Scan I'). Concurrently, the same relative motion is being experienced by detectors III', V', VII', and IX'. The relative movement of the even numbered detectors is represented by detector II'. As the "second half" of the scan is completed, detector II' moves from the position II'$_S$ in and over to the position II'$_F$ where the "second half" of the focal point scan for detector II is completed FS$_{II}'$ (Full Scan II'). FIG. 4(c) also illustrates schematically the focal point scan provided by each of the six "inward" moving detectors II', IV', VII', VIII' and X. The scan shown is provided, for the respective detector, along the respective radial angle indicated, i.e. $\alpha_{II}\alpha_{IV}$-—$\alpha_X$. A similar presentation is shown in FIG. 4(d) for the six "outward" going detectors I', III', V', VII' and IX'. As is representatively illustrated in FIG. 5, any point in the transverse section Z is focal point scanned twice by at least one half of the total detectors, i.e., at least 5 detectors in the presently considered embodiment and in effect is scanned by at least ten detectors. Because of overlaps the central region is scanned by up to 10 detectors, and in effect by up to 20 detectors. This overlap, which is provided by all detectors in the preferred embodiment of the present invention, permits convenient equalization and normalization of the detectors. FIG. 5 shows a focal point scan for an "outward" going detector, e.g., detector VI where $\theta=0°$, and provides, for a twelve line scan, typical dimensions for scan line length (20.48 inches), spacing (0.96 inch), resolution elements (128 per line) and the like. As shown in FIG. 5, the exemplary point "R" is "focal point scanned" twice by the five detectors VI, VII, VIII, IV and V and is effectively scanned by ten detectors. FIG. 5(a) is based on FIG. 5 and shows the detectors which scan two arbitrarily chosen points in the scan field which are scanned twice by five detectors; FIG. 5(b), also based on FIG. 5, shows the central region of the scan where scanning by up to twenty detectors (I-X, I'-X') occurs. The numbers in FIG. 5(b) show on the same basis the effective number of detectors which scan the indicated region; the same type of information for any point in the scan field can be routinely determined from grids of this type in relation to the position of the detectors.

In the course of a transverse focal point scan as described above, each detector continuously receives the emitted radiation, e.g., gamma photons appearing within the included angle of the collimator and this radiation is converted into counts by the associated scintillation crystal and photomultiplier tube of each detector. Electrical signals provided by respective photomultiplier tube can be conventionally amplified, detected by pulse amplitude discrimination techniques, identified as to spatial orientation in the scan field and, in the form of digital numbers corresponding to counts and detector position, transferred to the memory of a general purpose computer. The stored information thus provided is, on account of using highly focused collimators in accordance with the present invention, readily reconstructed to provide a high sensitivity quantification and spatial location of the radioactivity in the transverse section which is focal point scanned. This is so since focusing collimators inherently sum the counts from each point, and by focal point scanning in and out as well as tangentially, the combination of collimators cover (sum) substantially 360° about each point in the transverse scan. The counts thus collected are predominantly counts originating at the focal points of the collimators but also include (convolved with) some counts from "out of focus points". These unwanted counts can be removed by deconvolving the stored information with a filter function $r^{-k}$ (k>1) by a relatively simple algorithm such as taking a Fourier transform of a ramp in frequency space; for example, as described in "The Fourier Reconstruction of a Head Section"—L. A. Shepp, B. F. Logan "IEEE Transactions on Nuclear Science" Vol. NS-21, June 1974. The resulting reconstructed data is then available for display showing quantified and spatially oriented radioactivity. Other known techniques can also be used to remove the unwanted counts.

The concept of using highly focused collimators for this purpose is based on the recognition that the Radon* equation, can be put in a form that demonstrates that reconstruction using the counts summed (collected) over nearly 360° is possible.

With reference to FIG. 6

RADON:
$$G(R,B) =$$

$$\frac{1}{2\pi^2} \int_{-\frac{\pi}{2}}^{+\frac{\pi}{2}} \int_{-\infty}^{\infty} \frac{\partial F(P,A)}{\partial P} \cdot \frac{1}{R \sin(B-A) - P} \, dP \, dA =$$

$$\frac{1}{2\pi^2} \int_0^{\pi} dA \int_{-\infty}^{\infty} \frac{dF(P,A)}{dP} \cdot \frac{1}{R \sin(B-A) - P} \, dP$$

To reconstruct a point at the origin:

$$G(o) = -\frac{1}{2\pi^2} \int_0^{\pi} dA \int_{-\infty}^{\infty} \frac{dF(P,A)}{P}$$

LET $dA = \Delta A$, $Am = m\Delta A$     $M = $ number of projections $(\pi/\Delta A)$ $dP = D$, $P = \eta D$ Replacing Derivative by Difference, $$G(o) = \frac{\Delta A}{2\pi^2} \sum_{m=1}^{M} \sum_{n=N}^{N} \frac{F[(n+1)D, m\Delta A] - F[nD, m\Delta A]}{\left(\frac{nD + (n+1)D}{2}\right)}$$

SINCE $\frac{\Delta A}{\pi} \sum_{m=1}^{M} \bar{F}(m\Delta A) = \bar{F}(\ )$ The average of $\bar{F}(\ )$ over all angles AND $\frac{nD + (n+1)D}{2} = \frac{D}{2}(2n + 1)$ $$G(o) = -\frac{1}{2\pi} \cdot \frac{2}{D} \sum_{n=-N}^{N} \frac{\overline{F}[(n+1)D] - \overline{F}(nD)}{2n+1} =$$

$$-\frac{1}{D\pi} \left( \underbrace{\frac{\overline{F}(D) - \overline{F}(o)}{1}}_{(n=o)} + \underbrace{\frac{\overline{F}(2D) - \overline{F}(D)}{3}}_{(n=1)} + \underbrace{\frac{\overline{F}(o) - \overline{F}(-D)}{-1}}_{(n=-1)(n=2)} + \ldots \right)$$

$$(n = -2)$$

$$= \frac{1}{D\pi} \left( \overline{F}(o) + \frac{1}{3}[\overline{F}(D) + (\overline{F}(-D)] + \frac{1}{15}[\overline{F}(2D) + \overline{F}(-2D)] + \ldots \right)$$

$$G(o) = \frac{4}{D\pi} \left( \frac{\overline{F}(o)}{2} - \sum_{n=1}^{N} \frac{\overline{F}(nD)}{(4n^2-1)} - \sum_{n=-N}^{-1} \frac{\overline{F}(nD)}{(4n^2-1)} \right)$$

In the final equation above $\overline{F}(o)$, $\overline{F}(nD)$ are simply the total counts directly measured by collimators and associated detectors.

With reference to FIG. 7, and the previous description and as hereinafter more fully described, each focal point scan line of each detector I-X, I'-X', is divided into 128 resolution elements, the location of which in the scan field is derived routinely from the mechanism of the gantry scan drive hereinafter more fully described. As a detector passes through a resolution element, accumulator 810 accumulates counts from the detector photomultipliers for the time of detector travel through the resolution element. For example, for a typical resolution element travel time of 80 milliseconds, the accumulator will receive the counts developed by the detector photomultiplier at 5μ second intervals which have an acceptable pulse amplitude as established by a pulse amplitude discriminator circuit in combination with an associated detector. As hereinafter more fully described, when the counts for a given resolution element have been received by the accumulator 810, this data is transferred to general purpose computer 840 for storage at an address corresponding to the spatial location, i.e., a grid is established in which, for each resolution element in the grid, the corresponding count data representing a quantification of collected counts is stored.

The stored data is then processed by an algorithm, preferably as described above, which provides data for display as exemplified in FIG. 8.

In the preferred embodiment of the present invention involving 12 scan lines per detector with 128 resolution elements per line, the scintillation count data from all of the detectors I-X, I'-X', involving 12 scan lines per detector with 128 resolution elements, per line, is stored at contiguous memory locations with the scan line data for each pair of opposed detectors being stored at contiguous memory locations in a manner which makes it appear that the opposing detectors travel in the same direction, as hereinafter described. This compensates for the opposite travel of opposed detectors. Each scan line is processed by the computer under program control deconvolving the stored information as previously described; since each opposing detector scans 12 lines, but 2 of these lines overlap, as previously mentioned, a merged 22×128 array is produced, one for each detector pair. The merged arrays are then summed into one 128×128 array taking into account the angular ($\theta = 0°$ or $\theta = 18°$) orientation of each array. The result is stored and is available to make a picture display.

With reference to FIGS. 9—9(o), these figures show, in conjunction with FIGS. 10(a)-10(d), a novel and preferred means for providing the 360° focal point scanning hereinabove described. FIG. 9(a) is an isometric assembly view showing a gantry 4 to which is attached a frame assembly 50 comprising a rear frame plate 52 and a front frame plate 54, each suitably of aluminum ribbed casting. The opposed front and rear frame plates 54, 52 are joined by means of lateral rods 56 to form frame assembly 50. Rear frame plate 52 of frame assembly 50 is affixed to a ring 58 by bolts 60 and is rotatably supported on horizontal support member 62 in ring bearing 64 which is attached to support member 62 as shown more fully in FIGS. 9(e) and 9(f). Five tracking assemblies 65 are mounted on the inner surface of rear frame plate 52 at a common radial distance from axis Y at equal radial angle intervals of 72° as shown more clearly in FIG. 9(b). Five similar tracking assemblies 67 are mounted on the opposing inner surface of front frame plate 54, as shown more clearly in FIG. 9(c), at the same common radial distance from axis Y at equal radial angle intervals of 72°, but radially offset from the rear plate tracking assemblies 65 by a radial angle of 36° so that all of the rear plate tracking assemblies 65 and front plate tracking assemblies 67 are displaced from each other by an equal radial angular interval of 36°, as are detector assemblies I-X mounted in channel supports 70 which are alternately fixedly engaged to tracking assemblies 65, 67. The focal points of the collimators 30 of detectors I-X lie in a common plane transverse to axis Y. As shown in FIG. 9(b), (and in FIG. 9(c)) the reference angle "0" in FIGS. 4(a)-4(d) is offset from the vertical by 9°. This offset does not affect the scanning effectiveness of the apparatus and is for the purpose of mechanically facilitating the 18° rotation of frame 50 hereinafter described.

With further reference to FIG. 9 a cage member 72, shown further in FIGS. 9(d) and 9(e) formed of opposed rear ring 74 and front ring 76, joined by lateral supports 78, is rotatably mounted within and with respect to frame assembly 50 on a plurality of rollers 80 which are mounted on rear frame plate 52 and front frame plate 54. Drive block assembly 77, slidably mounted on rail assembly 63, and including slotted slide rod 31 engaging rollers 33 mounted on plate 71, pivotally engages at 79, the front ring 76 of cage member 72, through ring extension member 81 affixed to front ring 76. Arms 83, pivotally mounted to rear ring 74 at 85 engage back plate tracking assemblies 65, and arms 87, pivotally mounted to front ring 76 of cage member 72 at 89, engage front plate tracking assemblies 67. Upon actuation of stepping motor 98, which is fixed to front frame plate 54 by way of rail assembly mount 63, belt drive 100 rotates coupled screw 102 and moves drive block assembly 77 and slide rod 31 which causes cage member 72 to rotate, with respect to frame assembly 50 on rollers 80, 82 and impart tangential motion, in the same rotational sense to all carriage mounts 104 along rails 106 by way of pivoted arms 83 and 87. As shown in FIG. 9 and more clearly shown in FIG. 9(b) in conjunction with FIG. 9(i)-9(k) plurality of coupled screws 82, displaced by a radial angle of 72°, are rotatably mounted on rear frame plate 52 at brackets 142, 144 and engaged to each rear plate tracking assembly 65 and, with further reference to FIG. 9(c), radially displaced by 72°, a plurality of coupled screws 84 are similarly rotatably mounted on the back of front frame plate 54 and engaged to each front plate tracking assembly 67; the coupled screws 84 of front frame plate 54 are offset from coupled screws 82 of rear frame plate 52 by a radial angle displacement of 36°. A stepping motor 86, mounted on rear frame plate 52, with further reference to FIGS. 9(f), 9(g), 9(i) and 9(n) is connected by a belt drive 88 to the adjacent coupled screw 82, which engages the tracking assembly 65, on rear frame plate 52, for detector I. Actuation of this stepping motor 86 causes rotation of the bevel gear 90 engaged to screw 82 and incremental radial motion of tracking assembly 65 for detector I. The rotation of bevel gear 90 causes adjacent bevel gears 91 to rotate in an opposite sense such that each of the ten bevel gears rotates in the opposite sense to its adjacent bevel gears. The bevel gears 91, adjacent to bevel gears 90 are engaged to un-threaded rotatable shafts 94 which are mounted on rear frame plate 52 displaced from the coupled screws 82 by a radial angle of 36°. The non-threaded shafts 94 engage, by cross-over belt drives 96, opposite coupled screws 84 which are mounted on front frame plate 52 and engaged to the front plate tracking assemblies 67.

Horizontal support member 62, shown more clearly in FIG. 9(f) on which frame assembly 50 is supported at ring bearing 64, is engaged to gantry 4 at pivot mounts 108, and, with reference to FIG. 9(n) during a scanning operation, is maintained either vertically upright, or at an angle of ±15° to the vertical, by means of motor driven piston rod 110, pivotally attached to gantry 4 at 112, and plate 114, fixedly attached to frame assembly 50 at 116 and pivotally connected at 118 to piston rod 110 of motor 111.

Referring again to FIG. 9 the frame assembly 50 and the array of detectors I-X mounted thereon is rotatable on bearing 64 through an 18° (θ) rotation by actuation of stepping motor 120 and coupled screw 122 which are mounted on frame 124 as shown particularly in FIGS. 9(f), 9(g), 9(n) and 9(o), screw 122 being free to rotate in bearing 159 on frame 124. Frame 124 is pivotally mounted at 125 on trunnion 126 which is fixedly mounted to horizontal support member 62 and drive block 128, which is threadably engaged to motor driven screw 122, pivotally engages rear frame plate 52 as shown at 130 and more clearly shown in FIG. 9(o). With reference to FIG. 9(o) block 128 is affixed to a shaft 129 which is free to rotate in sleeve bearing 131 of flange 133 and aperture 143 in rear frame plate 52. Flange 133 is fixed to rear frame plate 52 by bolts 148. Consequently, movement of block 128 along screw 122, due to rotation of screw 122 by motor 120, causes rear frame 52, and hence frame assembly 50 and the detectors I-X, to rotate on ring bearing 64. Thus, with block 128 at position 150 shown in FIG. 9(f), the frame assembly 50 is in the positions shown in FIGS. 9(b) and 9(c) and 10(a) and 10(b). Upon actuation of motor 120 by a suitable signal from a microcomputer or otherwise, block 128 is moved along screw 122 to position 151 shown in FIG. 9(g) and the frame 50 is rotated through θ = 18° to the position shown in FIGS. 10(c) and 10(d). FIG. 4(a) illustrates the position of detectors I-X for θ = 0°, FIG. 4(b) shows the position of the detectors for θ = 18°; while the angle of rotation θ for FIG. 4(b) is clockwise as compared to counter-clockwise in FIG. 10(d) the effective scanning is the same.

The tracking assemblies hereinabove described are more fully illustrated in FIGS. 9(i), 9(j) and 9(k); the foregoing figures are described in connection with a back plate tracking assembly 65 but the description is equally applicable, except for bevel gear operation, to a front plate mounted assembly 67. Referring to FIGS. 9(i)-9(k), tracking assembly 65 includes rail 106 fixed to a mount 134 along which carriage mount 104, by way of affixed block 105, travels during the scanning motion hereinafter described. Mount 104 is provided with rollers 136 which engage the slots 99 in arm 83 which is pivotally engaged at 85 to the rear ring 74 of cage member 72. Mount 134, by way of affixed blocks 135, slidably engages rail 138 which is fixed to rear frame plate 52, parallel and adjacent to screw 82, as shown at 140, and mount 134 travels radially on rail 138 during the scanning motion hereinafter described. Rollers 137 mounted on blocks 139 affixed to carriage mount 104 engage guide 141 affixed to mount 134 and rollers 143 on mount 134 contact tracks 145 on rear frame plate 52. Coupled screw 82, rotatably mounted on rear frame plate 52 in brackets 142, 144 engages mount 134 at flange 146 and when driven, causes mount 134, and carriage 104 to travel in a radially inward or outward direction, depending on the rotation of screw 82, on rail 138. FIG. 9(i) shows the illustrated tracking assembly in a "half-way" position of a scan with arm 83 directly opposite screw 82 and the shaft of bevel gear 90.

With reference to FIGS. 10(a) and 10(b), these views show, for θ = 0°, in FIG. 10(a), the rear frame plate 52 and the tracking assemblies 65 and detectors I, III, V, VII and IX mounted thereon, and in FIG. 10(b) the front frame plate 54 (looking from the back) and the tracking assemblies 67 and detectors II, IV, VI, VIII and X mounted thereon. In FIG. 10(a) all tracking assemblies 65 are in "full out" position, and in FIG. 10(b) the radially opposed tracking assemblies 67 are in the "full in" position, representing the start of a scan. For the conditions shown in FIGS. 10(a) and 10(b), at the start of a scanning operation, with reference to FIG. 9(l), stepping motor 98, mounted on the front of front frame plate 54 drives coupled screw 102 by way of belt drive 100 which causes engaged drive block 77 to move along rail 103 from position 77' to position 77" in the direction indicated. The slideable arm 81 of drive block 77 is pivotally fixed at 79 to front ring 76 of cage member 72 to which pivoted arms 83 and 87 are connected, and cage member 72 is rotated, with respect to plates 52 and 54, i.e., frame 50, an amount which causes arms 83 and 87 to be linearly displaced a distance equal to a scan line. Consequently, each of the carriage mounts 104, and the detectors I-X supported thereon, move simultaneously in the same tangential direction, e.g., counter clockwise as shown at 88 in FIG. 9(l), a distance of scan line. Thus, considering the position of tracking assemblies 65 in FIG. 10(a) and 67 in FIG. 10(b) to represent the beginning of a scan, stepping motor 98 is energized to drive motor 98 is energized to drive coupled screw 102 whereby drive block 77 moves from position 77' to position 77" shown in FIG. 9(l), e.g., a distance of 20.48 inches shown at 400 in FIGS. 9(l), 10(a) and 10(b). This distance is translated through the rotation of cage member 72 into a travel of 20.48 inches for each of the carriage mounts 104 and detectors I–X. This travel is such that all detectors I–X move at the same time, counterclockwise (viewed from front frame 50) the same tangential distance 400 which is equal to a scan line as shown in FIGS. 4(a)–4(d) and FIGS. 10(a) and 10(b), with a predetermined number of steps of travel being a scanning resolution element, as hereinabove described, typically 1/128 of the scan line distance 400. When the tangential detector movement travel of 400 of the detectors I–X along rails 106 has been completed, a signal is provided, e.g., from a microcomputer, or otherwise, which actuates stepping motor 86, which is engaged to coupled screw 82 by belt drive 88, and to gear 90. The above-described linkage is arranged such that a number of steps of motor 86 causes coupled screw 82 to move the engaged mount 134 of the indicated tracking assembly 65 for detector I inward, a distance equal to the desired scan line separation shown as 450 in FIG. 10(a). Concurrently, the adjacent bevel gears 91, rotate oppositely to bevel gear 90, and this rotational motion is transferred by cross-over belt drives 96 to an opposed coupled screws 102' on front frame plate 52 which engage mount 134' of front plate mounted tracking assemblies 67 for detectors II, IV, VI, VIII and X shown in FIG. 10(b). The other bevel gears 90' for detectors III, V, VII and IX, rotate in the same direction as the motor driven bevel gear 90 for detector I. Consequently, with reference to FIG. 10(a), when the mounts 134 for back plate mounted detectors I, III, IV, VII, and IX move inward a scan line separation distance 450, the carriages 134' for front plate mounted detectors II, III–IX, with reference to FIG. 10(b); move outward a scan line distance 450'. At this time, an appropriate signal to stepping motor 98 causes coupled screw 102 to rotate opposite to its first direction and the travel of block 77 occurs as before, but now in the opposite direction, from 77" to 77'. Due to this reversed motion of block 77 cage member 72 rotates in a reversed direction (dotted lines in FIG. 9(l) and the linear movement of pivoted arms 83 and 87 and detectors I–X is reversed. A second scan line, opposite in direction to the first scan line is thus provided for all of the detectors I–X and stepping motor 86 is re-actuated and the radially inward and outward movement of the detectors, as previously described, is repeated. This cycle of operation is continued until the "first half" of a scan indicated in FIG. 4(a) is completed.

At this time, the detectors I–X of FIGS. 10(a) and 10(b) have moved to the dotted positions $I_F$–$X_F$ and motor 120 is actuated to rotate frame assembly 50, in bearing 64 an angular displacement of $\theta = 18°$ to the position shown in FIG. 9(l). Due to this 18° rotation, the detectors $I_F$–$X_F$ are positioned as shown, $I'_S$–$X'_S$ in FIGS. 10(c) and 10(d). Upon being positioned as shown in FIGS. 10(c) and 10(d), the above described scanning cycle is repeated except that detectors I, III, V, VII and IX are moved incrementally radially outward at the end of each scan line while the other detectors II, IV, VI, VIII and X more readily available. Upon completion of which scanning cycle a full scan is completed with the detectors in the positions shown at I–X in FIGS. 10(c) and 10(d).

In the apparatus of the present invention described above the scan line direction is explained as a movement of a tracking assembly, tangential to the scan area in the center of the apparatus. The prime mover for the scan line motion, is a single stepping motor which turns a screw which moves a drive block along a rail. The drive block is connected by a slotted arm pivotally attached to a rotatable cage member which engages, by pivotally connected slides, the carriages of all tracking assemblies mounted on a frame. The cage member is supported by a rollers on the frame on which the tracking assemblies are mounted which allows the cage to rotate when driven by the drive block. The slides pivotally engaged to the cage convert the rotary motion of the cage to linear motion of the carriages of the tracking assemblies and synchronize the motion of all the carriages of the tracking assemblies, and the speed and location of the carriages of the tracking assemblies are proportional to the speed and location of the drive block. The "in-out" direction is the radial motion of a tracking assembly with respect to the circular scan area. When a scan-line movement has been completed, that is, when the carriages on the tracking assemblies have moved from one extreme position to the opposing extreme position, the "in-out" prime mover, a second stepping motor, turns a screw which moves one outer tracking assembly some unit distance away from the center of the scan area. The screw that moves that one outer tracking assembly is mounted a bevel gear—in the drawing a 36° bevel gear. This bevel gear drives nine other 36° bevel gears which form a complete circle. The two bevel gears on either side of the drive bevel gear will rotate in the opposite direction of the drive bevel gear. The driven bevel gear, and alternate bevel gears are attached to drive screws mounted on the rear plate of the frame assembly which drive attached rear plate mounted tracking assemblies. The other alternate bevel gears are attached to drive shafts mounted on the rear plate of the frame assembly and communicate by belt drives with opposed drive screws mounted on the front plate which drive the front plate mounted tracking assemblies. When the "in-out" prime mover causes a rear plate mounted tracking assembly to move outward one unt of distance, the bevel gear assembly causes the adjacent rear plate mounted tracking assemblies and the radially opposite front plate mounted tracking assembly to move inward one unit of distance. Since all the movement of the tracking assemblies are mechanically connected together and controlled by only one prime mover for each direction, there is no possible error in electronic signal or component failure that could cause any of the detectors, mounted and moved by the tracking assemblies, to collide with one another. The unique movement in the "in-out" direction of a tracking assembly moving outward while the adjacent and radially opposite assemblies move inward allows for an efficient packaging of the large number of detectors utilized in the present invention. More important, it allows for the shortest possible focal distance for the large number of detector collimators involved, and the angular spacing of about 36° between the collimators remains constant throughout the scanning operation.

The general operation of the arrangement of FIG. 11 involves a computer 840 under program control which transmits memory address locations and commands, (address first followed by a command) through computer bus interface 843. The accumulator 810 receives commands from the scanner data multiplexer 820 by way of UART 870 and UART 879 and transfers scintillation count data and other data, by way of UART 879 and UART 870 to the scanner data multiplexer 820 for appropriate addressing and transfer to computer 840, for example a Data General Exlipse S230 general purpose computer under program control. Motor Control Microcomputer 890, hereinafter described and shown in FIG. 11(f) receives commands from the scanner data multiplexer 820 by way of UART 870 and UART 879 through command register and decoder 891 and issues commands to motor drivers 822, 823, and 824 and to the accumulator 810. Timing diagrams for reference in connection with FIGS. 11 to 11(e) are shown in FIGS. 11(a), 11(b) and 11(c); the scanner data multiplexer 820 is shown schematically in FIG. 11(d). The computer 840 processes the scintillation count data under program control as hereinbelow described.

Scanner data multiplexer 820, under program control in computer 840, sends commands to data acquisition circuits for purposes of (1) controlling detector movement via motor control microcomputer 890 (2) controlling couch movement via motor control microcomputer 890 and (3) performing diagnostics. It receives from the data acquisition circuits (1) accumulated scintillation count data (2) system status information and (3) diagnostic data. The scanner data multiplexer 820 calculates addresses for data to be deposited in computer memory in a method which optimally organizes the data in the high speed random access memory for further processing by the computer.

The scanner data multiplexer 820 provides bi-directional communication between a general purpose stored program computer and (1) circuits in the scanner system which drive motors to control the location of detectors and the patient via the motor control microcomputer 890 and (2) circuits in the system which accumulate scintillation counts from the detectors. The full duplex communication is implemented serially using a universal asynchronous receiver/transmitter interface (UART 870).

An exemplary communication format between the scanner data multiplexer 820 and the accumulator 810 and motor control microcomputer 890 via command register and decoder 891 is shown below in Table A.

TABLE A

| Code | Command |
|------|---------|
| 0001 | System Reset/Body Mode |
| 0010 | Start Scan Line/Patient Data Mode |
| 0100 | Start Scan Line/Data Diagnostic Mode |
| 0101 | Start Scan Line/Address Diagnostic Mode |
| 0111 | Scanner Data Multiplexer Internal Test |
| 1000 | Calibrate Gain Adjust |
| 1001 | Couch Movement |

All of these commands are transmitted from the scanner data multiplexer 820 in eight bit bytes via the UART 870. The first five commands are transmitted in one byte with the format shown in FIG. 14(a).

The last three commands are two byte commands and are transmitted in the format shown in FIG. 14(b).

All commands transmitted from the scanner data multiplexer 820 have been sent to it by the host computer 840 and are received on the computer bus 843 by the scanner data multiplexer 820 in the formats shown in FIG. 14(c).

Prior to transmitting a command, the scanner data multiplexer has received from the host computer 840 and has stored in its base address register 910 the starting address in computer memory for storing the status information and data which are received by the scanner data multiplexer 820 in response to the command.

Command and basic address information is recognized and accepted by the scanner data multiplexer 820 only when the device code decoder 821 decodes its predetermined device code as shown in bits 10-15 of FIG. 14(c).

If the command was a command to gather patient data or run diagnostics, the scanner data multiplexer, 820, upon receipt of the scanner data calculates an address for each transmission it receives. The format of the data received by the scanner data multiplexer 820 is of the form shown in FIG. 14(d).

Status and error messages are loaded into the address in computer memory which is stored in the base address register 910 of the scanner data multiplexer 820.

Data associated with one of the detectors is loaded in to a $2560_{10}$ word buffer in the computer main memory. All transfers from the scanner data multiplexer 820 into computer memory are via direct memory access. At the conclusion of transferring data into computer memory, the scanner data multiplexer 820 issues an interrupt request to the host computer 840 to notify the computer that the data deposited in computer memory is available for further processing.

The detector related data coming into the scanner data multiplexer 820 is associated with two channels from each of ten detectors. The sequence of data is such that the data for one resolution element from one channel of each of the ten detectors is received by the scanner data multiplexer 820.

Detector data is received sequentially from opposing detector pairs so that the sequence of detector data coming into the scanner data multiplexer 820 is as follows:

| | |
|---|---|
| CH 1 | Detector I |
| CH 1 | Detector VI |
| CH 1 | Detector II |
| CH 1 | Detector VII |
| CH 1 | Detector III |
| CH 1 | Detector VIII |
| CH 1 | Detector IV |
| CH 1 | Detector IX |
| CH 1 | Detector V |
| CH 1 | Detector X |
| CH 2 | Detector I |
| CH 2 | Detector VI |
| CH 2 | Detector II |
| CH 2 | Detector VII |
| CH 2 | Detector III |
| CH 2 | Detector VIII |
| CH 2 | Detector IV |
| CH 2 | Detector IX |
| CH 2 | Detector V |
| CH 2 | Detector X |

The address calculation circuits in the scanner data multiplexer 820 calculate addresses so that the same resolution element from each detector has a displacement in the 128 word buffer, associated with that detector, which corresponds to its displacement in the physical scanning pattern regardless of detector number or radial scanning step.

To accomplish this, two aspects of the detector motion patterns must be taken into account in calculating the correct location in computer memory for storing a resolution element: opposing detectors scan in opposite tangential directions so that while incrementing the address for one detector, the address for the opposing detector is decremented or vice versa; the motions of all detectors are reversed for each radial increment in gathering data so that after each radial step the incrementing/decrementing patterns are reversed. During all of these operations, an appropriate offset must be included in the address calculation to provide for offsetting the data for each buffer by 128 locations in computer memory.

With reference to FIG. 11, the detectors I to X are schematically shown in a line, with the direction of tangential travel for each detector indicated by the arrows above the detectors. The number "1" adjacent to the arrows indicates the first resolution element for the respective detectors while the number "128" indicates the last or 128th resolution element, in the preferred embodiment described herein. In operation, the scintillation developed by crystals 32 is converted to "counts" in photomultipliers 36, with discrimination being provided in pulse height analyzers 33 and a digital signal is delivered to high speed digital switch 800 which samples both channels of all detectors I–X during an interval of, for example about 5 μsec., so that on the order of 10,000 samplings of the detectors I–X occurs during a resolution element. Two independent channels are provided in the pulse height analyzers 33 to provide capability for situations where a patient has been administered two isotopes of different radioactivity energy levels. In such an instance, the data for both conditions can be separately and concurrently spatially and intensity oriented and displayed spatially.

The binary data obtained by sampling is passed to accumulator 810, containing for example, a RAM memory, which accumulates the data in a sequence of detectors I–X and transfers the data in a sequence of opposing detectors. For example, the sequence of transferred accumulated data can be detector I, detectors VI, II, VII; III, VIII, IV, IX; V, X. Upon completion of a resolution element of travel for each detector, i.e. 1/128 of the scan line, the contents of the accumulator 810 upon command of microcomputer 890 are transferred into the scanner data multiplexer 820 wherein the data is received serially in the sequence of opposing detectors as described above, and addressed to the memory 830 of the general purpose computer 840 at contiguous buffer memory locations, as hereinafter described, in an orientation such that the opposite and reciprocal motion of opposed detectors, is compensated.

At the end of a scan line, (i.e., 128 resolution elements for each of the ten detectors with two channel per detector), the words in the buffer memory locations are transferred to a magnetic disk and on completion of all the scan lines, e.g., 12 for each of the 10 detectors in position $\theta=0$ and 12 for each of the 10 detectors in position $\theta=18$, the magnetic disk contains all the scan line data for one "slice" in a form which facilitates reconstruction and the display of a picture as hereinabove described. The universal asynchronous receiver/transmitter interface, UART 870, provides commands under computer program control for the execution of the operations indicated in which the advance to the next command is signalled when the previous command has been completed.

With reference to FIG. 12, which shows a relevant portion of the previously mentioned scanner data multiplexer 820 shown in FIG. 11(d), at the end of the first and every subsequent resolution element, the input data register 900 receives, from accumulator 810, a "burst" of 40 bytes from which it assembles 20 sixteen bit words—ten words from each channel. The information in each of these words is for example, as shown in FIG. 14(d). This, for each resolution element, is in the sequence of opposed detectors, e.g., I, VI, II, VII, etc., with channel 1 data being followed by channel 2 data for all detectors. At the time that this burst of data is received by input data register 900, a base address, determined by the computer 840 under program control is in the base address register 910. This base address will be considered to be "4000" for purposes of convenience but can be any place in a high speed random access memory where a sufficient number of sequential memory address locations are available, e.g., 2560 (128 resolution elements × 10 scan lines × 2 channels) in the specific embodiments described herein.

Considering the first resolution element 1, all detectors I–X are at the start of a scan line; adder 920 is at a level representing a 1 count whenever data is not being loaded into the memory address contained in the base address register. Detector counter 930 is at 0 for the first detector I in the sequence I, VI, II, VII, etc. and resolution element counter 940 is at 0 for the first resolution element. Thus, for this condition, the one count in the adder 920, which represents the relative address in this case, is added to the base address 4000 in adder 920 to establish an absolute address of "4001" in the abosolute address register 960. This address followed by the scintillation count data for detector I in input register 900, a sixteen bit word, is transferred via conventional address/data multiplexer 970 to memory 830 of computer 840. This transfer is via the computer's direct memory access channel for the presently described embodiments. With reference to FIG. 13, memory 830 comprises 20 storage buffers A, B, —K of 128 words each, for a total of 2560. For the first resolution element 1, the word representing the counts of the first detector in the sequence, detector I, are stored in the first address location of buffer A shown at "4001".

Detector counter 930 is incremented by one, which provides an offset of 128, the total number of resolution elements, upon the entry of the data for detector I into memory, as previously described.

For detector VI, the second detector in the sequence I, VI, II, VII, etc., detector counter 930 is at "1", being incremented upon the transfer of data from accumulator 810 and resolution counter 940 remains at "0"; for detector VI, (and every other subsequent detector in sequence, i.e., VII, VIII, IX and X) the complement control 945 provides the complement of resolution counter 940 in adder 920. Thus, for detector VI, the complement 127 is added to 128 from the incremented detector counter 930, and 1 in the adder 920, to give 256 which is added to the base address to provide an address of 4256 in address register 960. This address followed by the count data in input register 900, a sixteen bit word, is transferred to memory 830 of computer 840. This as shown in FIG. 13 illustrates that the word representing the counts of the second detector in the sequence, detector VI, are stored in the last address location of buffer B shown at 4256. For the next, i.e., third detector in the sequence, detector II, detector counter 930 has been further incremented by one, to provide an offset by 128 to 256, which is added to the 1 in adder 920, to provide a relative address of 257, complement control 945 being inactive for detector II, as in the case of detector I. The address location for the word representing the "counts" of detector II for the first resolution element is 4257, the first address location in buffer C. For detector VII, the next detector in the sequence, the detector counter 930 is further incremented one, to provide an offset by 128 to 384, which is added to the 1 in adder 920, and the complement 127, to provide a relative address of 512 for which the address location is 4512 the last address location in buffer D.

As can be seen, and with reference to FIG. 13, and Table B, the operation of scanner data multiplexer 820 provides for the loading of the adjacent buffers for opposing detectors from opposite directions. For example, the first word for detector I is loaded at the first address location in buffer A while the first word for the opposed detector VI is loaded in the last address in buffer B. The same opposite loading is seen for buffers C, D; E, F; G, H; J, K. At the end of the scan line, 128 resolution elements, all of the buffers A-K have been loaded in the manner described, as further shown in the exemplary Table B hereinbelow. Consequently, the contents of the memory 830 for a scan line can be transferred to a magnetic disk 855 in a sequence which constitutes a compensation for the opposite travel of the opposed detectors and subsequently processed by computer 840 as described hereinabove.

The above description was directed to the first of a plurality of scan lines, 12 in the embodiment being considered. For the second scan line, the detector travel is from resolution element 128 to 1 and for this scan line, the previously described interaction of adder 920, detector counter 930 and resolution element counter being incremented at the end of the scan line) except that complement control 945 provides a complement for the alternate detectors I, II, III, IV and V instead of VI, VII, VIII, IX and X.

That is to say, for the odd numbered scan lines, or odd numbered radial steps, first, third, etc., the complement control operation is the same; but the complement control is reversed for the even numbered scan lines.

The above description for data collection would apply whether the detector array was in position $\theta=0°$ or $\theta=18°$; detector data is received in the same sequence, addressed in the scan data multiplexer 820 to the buffer memory 830 of the general purpose computer 840 and words in the buffer memory locations are transferred to the magnetic disc memory of the general purpose computer 840 all in the manner hereinabove described.

Data is thus collected for the hereinbefore described construction at a slice in the following sequence: With the detectors I, II, —X in position $\theta=0°$, the scanning procedure hereinabove described is commenced. The first X direction scan line data (an odd radial Z-step) for each detector is addressed by the scanner data multiplexer 820 to the buffer memory 830 in the sequence described in conjunction with FIG. 13 and Table B. The ordered data for the 2560 resolution elements of the first X direction scan line is transferred to the disc memory of the general purpose computer 840 (128 resolution elements $\times$ 10 detectors $\times$ 2 channels per detector). Each ordered data element of the first scan line thus corresponds to a known position in the scan field and can be routinely related to a grid location of the entire scan field, as hereinabove described, by the program control of the general purpose computer 840. The ordered 2560 resolution elements for the second X direction scan line (even radial Z-step) is likewise placed in the memory of the general purpose computer 840. This procedure is continued until all twelve scan lines of each of the ten detectors I through X of the present embodiment are placed in the memory of the general purpose computer. Upon completion of the twelfth scan line, the ten detectors are rotated 18° (to position $\theta=18°$) as hereinabove described and represented as detectors I' through X' in the figures of the drawing. The detectors I' through X' start their first X direction scan line (odd radial Z-step) at the position where they completed their $\theta=0°$ scan with the resolution element data addressed to the buffer memory 830 of FIG. 13(a) and thence transferred to the disc memory of the general purpose computer 840, followed by the second X direction scan line (even radial Z-step), followed by the successive odd and even X direction scan lines until the completion of all 12 scan lines in the present embodiment for detector array position $\theta=18°$ in the same manner as for detector array position $\theta=0$. Thus the data for the 128 resolution elements for the twelve scan lines for the two channels of each of the ten detectors for position $\theta=0°$ and $\theta=18°$ is ordered in the disc memory of the general purpose computer so that the location of each data resolution element can be routinely related to a known grid position of the scan field to construct the slice hereinabove described.

TABLE B

| CH 1 REL Address LOC | DET I I.D.SEQ | CH 1 | DET II | CH 1 | DET III | CH 2 | DET IV | CH 2 | DET V |
|---|---|---|---|---|---|---|---|---|---|
| 1 | 1 | 257 | 3 | 513 | 5 | 2049 | 17 | 2305 | 19 |
| 2 | 21 | 258 | 23 | 514 | 25 | 2050 | 37 | 2306 | 39 |
| 3 | 41 | 259 | 43 | 515 | 45 | 2051 | 57 | 2307 | 59 |
| — | — | — | — | — | — | — | — | — | — |
| — | — | — | — | — | — | — | — | — | — |
| 127 | 2521 | 383 | 2523 | 639 | 2525 | 2175 | 2537 | 2431 | 2539 |
| 128 | 2541 | 384 | 2543 | 640 | 2545 | 2176 | 2557 | 2432 | 2559 |
| 129 | 2542 | 385 | 2544 | 641 | 2546 | 2177 | 2558 | 2433 | 2560 |
| 130 | 2522 | 386 | 2524 | 642 | 2526 | 2178 | 2538 | 2434 | 2540 |
| — | — | — | — | — | — | — | — | — | — |
| — | — | — | — | — | — | — | — | — | — |
| 254 | 42 | 510 | 44 | 766 | 46 | 2302 | 58 | 2558 | 60 |
| 255 | 22 | 511 | 24 | 767 | 26 | 2303 | 38 | 2559 | 40 |
| 256 | 2 | 512 | 4 | 768 | 6 | 2304 | 18 | 2560 | 20 |
| CH 1 | DET VI | CH 1 | DET VII | CH 1 | VIII | CH 2 | DET IX | CH 2 | DET X |

ODD RADIAL "Z" STEPS

TABLE B-continued

EVEN RADIAL "Z" STEPS

| CH 1 REL. Address LOC | DET I I.D.SEQ | CH 1 | DET II | CH 1 | DET III | CH 2 | DET IV | CH 2 | DET V |
|---|---|---|---|---|---|---|---|---|---|
| 1 | 2541 | 257 | 2543 | 513 | 2545 | 2049 | 2557 | 2305 | 2559 |
| 2 | 2521 | 258 | 2523 | 514 | 2525 | 2050 | 2537 | 2306 | 2539 |
| 3 | 2501 | 259 | 2503 | 515 | 2505 | 2051 | 2517 | 2307 | 2519 |
| — | — | — | — | — | — | — | — | — | — |
| — | — | — | — | — | — | — | — | — | — |
| 127 | 21 | 383 | 23 | 659 | 25 | 2175 | 37 | 2431 | 39 |
| 128 | 1 | 384 | 3 | 640 | 5 | 2176 | 17 | 2432 | 19 |
| 129 | 2 | 385 | 4 | 641 | 6 | 2177 | 18 | 2433 | 20 |
| 130 | 22 | 386 | 24 | 642 | 26 | 2178 | 38 | 2434 | 40 |
| — | — | — | — | — | — | — | — | — | — |
| — | — | — | — | — | — | — | — | — | — |
| 254 | 2502 | 510 | 2504 | 766 | 2506 | 2302 | 2518 | 2558 | 2520 |
| 255 | 2522 | 511 | 2524 | 767 | 2526 | 2303 | 2538 | 2559 | 2540 |
| 256 | 2542 | 512 | 2544 | 768 | 2546 | 2304 | 2558 | 2560 | 2560 |
| CH 1 | DET VI | CH 1 | DET VII | CH 1 | DET VIII | CH 2 | DET IX | CH 2 | DET XII |

The hereinbefore described detector motions, i.e., tangential motion (X scan), incremental motion normal to the Y axis (Z in-out increment) and 18° rotational orientation change (θ) can be controlled in the present embodiment by a motor control microcomputer 890 as schematically shown in FIGS. 11 and 11(f).

With reference to FIG. 11(f), the microcomputer 890 of FIG. 11 is more particularly described as having a computer processing unit (CPU) 1200 which can be an Intel Corporation microprocessor model 8085, a random access memory and timer (RAM) 1210 which can be an Intel Corporation model 8155, and three erasable and electronically reprogrammable read only memory units (EPROM) 1220, 1230, 1240 which can each be an Intel Corporation model 8755.

Upon receipt of commands from the general purpose computer 840, the CPU 1200 of the microcomputer 890 in conjunction with the RAM 1210 in accordance with the routinely derived programs in the three EPROM's 1220, 1230, 1240 computes and transmits signals which control the hereinbefore described movement of the detectors (I through X) in the X, and Z directions and θ orientation.

In a representative sequence of steps, the general purpose computer 840 will command the motor control microcomputer 890 to place the detectors in their initial scan position as shown in FIGS. 10(a) and 10(b). Upon its own internal program control, the motor control microcomputer 890, will cause the X-drive motor driver 822 to activate the X-drive stepping motor 98 and cause the drive block 77 to travel so as to contact microswitch 771, at which time block 77 backs off microswitch 771 a known incremental distance and comes to rest by the direction of the motor control microcomputer under program control. Detectors I through X are now in their "X" scan tangential translation start position. The motor control microcomputer 890 will next cause the Z drive motor driver 823 to activate the Z-drive stepping motor 86 causing the mount 134 of detector I to travel radially outward in the Z direction so as to contact microswitch 861 at which time the mount 134 of detector I backs off microswitch 861 a known incremental distances and comes to rest by the direction of the motor control microcomputer under program control. Detectors I through X are now in their Z radial translation start position and also in their "X" scan start position as hereinabove described. The motor control microcomputer 890 will next cause "θ" drive motor 824 to activate the "θ" drive stepping motor 120 causing frame assembly 50 to rotate so that tab 501 on rear frame plate 52 will contact microswitch 521 at which time frame assembly 50 backs off microswitch 521 and frame assembly 50 comes to rest by the direction of the motor control microcomputer under program control. All detectors I through X are now their θ=0 position.

The contacting of each of the above noted microswitches causes the "X", Z and θ locations of the detectors I through "X" to be placed at a known reference location. Such reference points are derived by routinely relating the known mechanical location of detectors I through X in the gantry to the location of the scan field with respect to the gantry mechanism. After establishing these reference location points, the microswitches are not contacted again during the normal scan cycle.

With detectors I through X in their "start" position, the system is ready to start scanning.

Upon receipt of a command from general purpose computer 840, the motor control microcomputer 890 will cause the X-drive motor driver 822 to activate the X-drive stepping motor 98 to cause the tangential translation of each of the detectors I through X as hereinabove described. The microcomputer under program control provides pulses to the motor driver with each pulse being equivalent to a step of the stepping motor and thus a known increment of travel. The number of pulses are counted and retained in the microcomputer memory so that the corresponding tangential locations of the detectors I through X are known to the microcomputer. Upon entry of the detectors into the scan field, the accumulator 810 is advised by the microcomputer to start the counting of data and the data collection process as hereinbelow described is commenced. Upon the completion of the required number of pulses which correspond to the number of steps of motor 98 required for an increment of travel equal to 1 resolution element, the accumulator 810 is advised by the microcomputer 890, which has been counting the pulses and storing them in memory, to transfer the scan data for the resolution element to the general purpose computer 840 as hereinbelow described. The accumulator 810 is so advised by the microcomputer 890 for each of 128 resolution elements of the tangential scan in the present embodiment. Upon the completion of the 128 elements of the tangential scan, the accumulator 810 is advised by the microcomputer to stop counting. The operation of the microcomputer in the present embodiment can be illustrated as follows: The length of a scan in the X direction tangential scan line is 20.48 inches. Upon receipt by the microcomputer 890 of the command from the general purpose computer 840 to start a scan, the microcomputer under program control will accelerate the detectors to a preselected scanning speed by means of pulses to X-drive motor driver 822 accelerating the motor 98 so that the pulses reach the rate required to maintain the selected detector scan speed when the detectors enter the predetermined scan field. Since each pulse to the stepping motors correspond to a known increment of travel the microcomputer by counting the pulses and retaining them in memory "knows" the location of each detector after the hereinabove described initialization procedure has taken place. Since all fixed dimensions are known, the microcomputer can be routinely programmed to carry out its motor control functions for selected scan speeds. With the detectors translating at the preselected scan rate upon entering the scan field, the accumulator 810 is advised by the microcomputer 890 to start counting data. In the present embodiment, 20,480 pulse corresponding to 20,480 motor steps corresponds to 20.48 inches of an X scan line. Thus 160 pulses corresponding to 160 motor steps would correspond to 1 resolution element where there are 128 resolution elements per scan line. Since the microcomputer is counting pulses, at the end of the number of pulses required for each resolution element, the microcomputer advises the accumulator 810 to transfer the count data for the resolution element for each detector to the general purpose computer 840 for data handling as hereinabove described. Upon completion of the last resolution element, 128 in the present embodiment the detectors are routinely decelerated by program control of the microcomputer 890 at a selected rate with the pulses being counted by the microcomputer so that the position of the detectors are still "known" by the microcomputer. The microcomputer under program control next causes the ten detectors to step in their respective hereinabove described Z directions, 0.96 inches in the present embodiment, by the transmission of pulses to the Z drive motor driver 823 and motor 86 with the pulses again being counted and corresponding to a known increment of travel. With Z direction motion completed, the detectors are in position to start the next X scan line upon receipt by the microcomputer 890 of a command from the general purpose computer 840 to start the next scan line. The location of all detectors are still known to the microcomputer due to the pulse count being retained in the microcomputer memory. The above described procedure is repeated for each of the remaining 11 scan lines in the present embodiment. Upon completion of the twelfth scan line, the detectors remain in their X and Z positions and the microcomputer 890 under program control causes the ten detectors to rotate to $\theta = 18°$ by the transmission of pulses to the "$\theta$" drive motor driver 824 and motor 120. Again, the microcomputer 890 counts pulse to the stepping motor 120 which pulses correspond to steps of the stepping motor 120 and thus to a known increment of travel so that the locations of all detectors continue to be retained in the memory of the microcomputer. With the array of detectors in position $\theta = 18°$, the detectors I through X are ready to start their next scanning sequence under the program control of the motor control microcomputer 890 upon receipt of commands from the general purpose computer 840.

The above description is illustrative of the functioning of the motor control microcomputer 890 in the present embodiment which function can be routinely programmed into the microcomputer. Control of the detector motions and determination of data resolution elements may also be provided for by any conventional manner known to the art.

In addition to the hereinbefore described calculation of absolute addresses for the scintillation count data, the scanner data multiplexer 820 has the capability to provide for checking out memory loading process, accumulations process and the motor control microcomputer.

In the case of checking out the memory loading process, the scanner data multiplexer 820, shown in FIG. 11(d) checks the ability to deposit a particular variable pattern in all of the 2560 memory locations used for storing scintillation counts data. In checking out the memory loading process, the command seven is received on the computer bus 843 in the format of FIG. 14(c). Twelve bits follows, which can be any pattern, e.g., all "zeros", all "ones" or a "checker board" of "ones" and "zeros". A base address calculated by the computer 840, e.g., "4000" is established in base address register 910. The command is a 16 bit word, first the address, then the command which is received in output data register 809. The test pattern is the last twelve of the sixteen bits. The command is decoded at 819 and the 16 bit word in two 8 bit bytes is transferred by an output data multiplexer 829 to UART 870. For this command code, a test data circuit turns the data around back into the UART 870 and then into the portion of scanner data multiplexer shown in FIG. 12 and this data is manipulated in the manner previously described in connection with FIG. 12.

This "checking" data, instead of having a detector identification, e.g., I, VI, II, VII, etc., followed by scintillation data, is received as "code 7" followed by the test pattern generated by the computer 840. This data is addressed and stored in the buffers A-K of the computer memory in the same manner as described above in connection with FIG. 12 and all 2560 of the memory locations can accordingly be checked for the test pattern.

For checking the accumulation process, the scanner data multiplexer 820 checks the ability of accumulator 810 to transfer data in the desired sequence of opposed detectors I-VI, II-VII, etc. In this instance the command "four" is received on the computer bus 843 in the format of FIG. 14(a), and is received in output data register 809. A base address, e.g., "4000" is established in base address register 910; calculated by the computer 840. The command is decoded at 819 and one 8 bit byte, (base address, code four) is transferred by an output data multiplexer 829 to UART 870 which transmits the command four to accumulator 810 which, when it receives a command four, causes a timing circuit to trigger a test circuit which feeds the accumulator 810. The accumulator 810 generates either a $2525_8$ or a $5252_8$ pattern for one PHA channel as determined by the timing circuit. The accumulator 810, in the present instance, accumulates data by adding "one" whenever the input thereto is true. The accumulated data is then transmitted via UART 870 to the scanner data multiplexer arrangement of FIG. 12 as in the case of actual operation as described previously in connection with FIG. 12; the first four bits of each word will be a detector identification "I", etc., in the sequence of opposing detectors, followed by 1280 words of 2-5-2-5 and 1280 words of 5-2-5-2. These data words are addressed and transferred to the buffers A-K and A'-K' shown in FIG. 13 and buffers A-K receive 1280 words of 2-5-2-5 and A'-K' receive 1280 words of 5-2-5-2 (or vice versa) as a check of the accumulation.

For checking the motor control microcomputer 890, the scanner data multiplexer 820 checks the ability of the X-drive counting function to count to 128 (from 0 to 127), the ability of the Z-drive counting function to count to 12 (0-11) and checks that the $\theta$ orientation function changes after completion of the 12th Z-drive increment. Thus counts are provided for the 2560 contiguous buffer locations as previously noted. In this instance, command "5" is received on the computer bus 843 in the format of FIG. 14(a) and is received in output register 809. A base address, e.g., "4000" is established in base address register 910; the command is decoded at 819 and one 8 bit byte is transferred by an output data multiplexer 829 to UART 870 which transmits the command "5" to the microcomputer via UART 879 and command register and decoder 891 which step the microcomputer 890 X-drive function from 0 to 127 and Z-drive function from 0-11 respectively. For command "5" this data, the state of these counters, is transferred to the output register of accumulator 810, where scintillation data would ordinarily go. The counter data is then transmitted via UART 870 to the scanner data multiplexer arrangement of FIG. 12 as in the case of actual operation as described previously in connection with FIG. 12; the first four bits of each word will be a detector identification "I", etc., in the sequence of opposing detectors, followed by 1280 words and another 1280 words, reflecting the state of the X, Z, and $\theta$ counting functions of the motor control microcomputer 890, for a total of 2560. These data words are addressed and transferred to the buffers A-K and A'-K' of FIG. 13 as a check of the motor control microcomputer 890 counting function.

In the general purpose computer hereinbefore mentioned with reference to FIG. 11, the Data Channel Control 1000, Interrupt Control 1002, Computer Data Output Control 1004 are conventional arrangements for arbitrating priority and providing interruptions.

FIG. 8 shows a display obtained through the practice of the above-described preferred embodiment of the present invention. The display shows a liver "slice" (#7), 5 minutes per slice with the radionuclide being 99 Tc.

Particular advantages of the imaging device of the present invention are the ability, due to the ultrahigh sensitivity provided, to permit early diagnosis of pathological changes and images can be obtained which show accurately the location and shape of physiological abnormalities. Images can be conveniently retrived and a plurality of transaxial slices can be readily obtained with each taking from 2-5 minutes. Further, high target to background images can be readily obtained with excellent functional detail due to the use of highly focused collimators in the manner of the present invention; in addition dual radionuclide pharmaceutical studies can readily performed simultaneously.

The mechanical implementation is such that the entire system can be accomodated in a 18'×16' room. Importantly, the scanning pattern with the use of highly focused collimators, enables the use of collimators of quite short focal length, i.e., the focal length need be only about ½ the diameter of the total scan field. Moreover, the continuous and essentially constant close adjacency of the highly focused collimators throughout the scanning operation enables optimum collection of patient emitted radiation, The above description has been particularly directed to the rotation of an array of collimators from a first scan position to a second scan position by an angle "$\theta$" which effectively doubles the number of collimators. It is possible with appropriate mechanical re-design to sequentially rotate the array of collimators by an angle which further multiplies the effective number of collimators. For example, with a ten collimator array, the effect of forty collimators is obtained by rotating the array 27°, in 9° sequences from its first scan position, to second, third and fourth scan position. The general expression is as follows:

(1) $\theta$ Sequence Angle = (360° ÷ no. of collimators) ÷ Desired Collimator Multiplication Factor.

(2) Total $\theta$ Rotation = (Multiplication Factor $-1$) × $\theta$ Sequence Angle.

What is claimed is:

1. A scanning apparatus for an array of highly focused collimators comprising a collimator support frame for supporting collimators in an inwardly focused array surrounding a scan field, said collimator supporting frame having opposed spaced apart support plates; a plurality of equally angularly spaced collimator mounts alternately moveably mounted on opposing surfaces of said support plates surrounding the scan field, said collimator mounts being moveable radially toward and away from the axis of said scan field; means for simultaneously moving all said collimator mounts such that alternate collimator mounts move in synchronism radially toward and away from the axis of the scan field; a plurality of carriage means, each moveably engaged to a respective collimator mount, being moveable on such respective collimator mount in a direction transverse to the said radial movement of such collimator mount, annular means rotatably mounted on said collimator support frame surrounding said scan field; a plurality of translating means each pivotally engaged to said annular means opposite and slidably engaged to a respective carriage means; means for rotating said annular means with respect to said collimator support frame to impart motion to each carriage means transverse to the radial movement of the collimator mount moveably engaged thereto; and means for rotating said collimator support frame a predetermined angular increment about the axis of the scan field.

* * * * *